US010213317B2

(12) United States Patent
Bishop et al.

(10) Patent No.: US 10,213,317 B2
(45) Date of Patent: Feb. 26, 2019

(54) IMPLANT WITH SUPPORTED HELICAL MEMBERS

(71) Applicant: Institute for Musculoskeletal Science and Education, Ltd., Wayne, PA (US)

(72) Inventors: Sean S. Bishop, Malvern, PA (US); Christopher J. Ryan, Lincoln University, PA (US); Edward J. McShane, III, Collegeville, PA (US); Megan A. Stauffer, Wayne, PA (US); Joseph M. Nyahay, Eagleville, PA (US)

(73) Assignee: Institute for Musculoskeletal Science and Education, Wayne, PA (US)

( * ) Notice: Subject to any disclaimer, the term of this patent is extended or adjusted under 35 U.S.C. 154(b) by 0 days.

(21) Appl. No.: 15/457,485

(22) Filed: Mar. 13, 2017

(65) Prior Publication Data

US 2018/0256361 A1 Sep. 13, 2018

(51) Int. Cl.
*A61F 2/44* (2006.01)
*A61B 17/88* (2006.01)
(Continued)

(52) U.S. Cl.
CPC ........ *A61F 2/4455* (2013.01); *A61F 2/30767* (2013.01); *A61F 2/442* (2013.01);
(Continued)

(58) Field of Classification Search
CPC .... A61F 2/4455; A61F 2/30767; A61F 2/442; A61F 2/4611; A61F 2002/30131;
(Continued)

(56) References Cited

U.S. PATENT DOCUMENTS

| 4,961,740 A | 10/1990 | Ray et al. |
| 5,458,638 A | 10/1995 | Kuslich et al. |

(Continued)

FOREIGN PATENT DOCUMENTS

| WO | 2009-051779 A1 | 4/2009 |
| WO | 2010-097632 A1 | 9/2010 |

(Continued)

OTHER PUBLICATIONS

International Search Report and Written Opinion for PCT application PCT/US2016/029865 dated Aug. 19, 2016.
(Continued)

*Primary Examiner* — Pedro Philogene
*Assistant Examiner* — David C Comstock
(74) *Attorney, Agent, or Firm* — Plumsea Law Group, LLC

(57) ABSTRACT

An implant includes a body including a peripheral frame portion defining a periphery of the body and a central wall extending from a first side of the peripheral frame portion to a second side of the peripheral frame portion. The implant may further include a first bone contacting member attached to the body and disposed within the superior half of the implant. Also, the implant may include a first support member extending from a first point on a superior side of the peripheral frame portion to the first the bone contacting member and further extending inwardly of the bone contacting member into a central region of the implant and terminating at a second point on an inferior side of the peripheral frame portion adjacent to the first point from which the first support member extends.

20 Claims, 22 Drawing Sheets

(51) Int. Cl.
*A61F 2/30* (2006.01)
*A61F 2/46* (2006.01)

(52) U.S. Cl.
CPC ..... *A61F 2/4611* (2013.01); *A61F 2002/3093* (2013.01); *A61F 2002/30131* (2013.01); *A61F 2002/30289* (2013.01); *A61F 2002/4475* (2013.01); *A61F 2002/4629* (2013.01)

(58) Field of Classification Search
CPC .... A61F 2002/30289; A61F 2002/3093; A61F 2002/4475; A61F 2002/4629
USPC .......................................... 623/17.11, 17.16
See application file for complete search history.

(56) References Cited

U.S. PATENT DOCUMENTS

| | | | |
|---|---|---|---|
| 5,571,192 | A | 11/1996 | Schonhoffer |
| 5,607,424 | A | 3/1997 | Tropiano |
| 5,609,635 | A | 3/1997 | Michelson |
| 5,658,337 | A | 8/1997 | Kohrs et al. |
| 5,709,683 | A | 1/1998 | Bagby |
| 5,716,416 | A | 2/1998 | Lin |
| 5,897,556 | A | 4/1999 | Drewry et al. |
| 6,039,762 | A | 3/2000 | McKay |
| 6,090,143 | A | 7/2000 | Meriwether et al. |
| 6,126,689 | A | 10/2000 | Brett |
| 6,149,651 | A | 11/2000 | Drewry et al. |
| 6,200,348 | B1 | 3/2001 | Biedermann et al. |
| 6,206,924 | B1 | 3/2001 | Timm |
| 6,371,987 | B1 | 4/2002 | Weiland et al. |
| 6,428,575 | B2 | 8/2002 | Koo et al. |
| 6,436,141 | B2 | 8/2002 | Castro et al. |
| 6,494,883 | B1 | 12/2002 | Ferree |
| 6,500,205 | B1 | 12/2002 | Michelson |
| 6,520,996 | B1 | 2/2003 | Manasas et al. |
| 6,527,805 | B2 | 3/2003 | Studer et al. |
| 6,537,320 | B1 | 3/2003 | Michelson |
| 6,582,467 | B1 | 6/2003 | Teitelbaum et al. |
| 6,585,770 | B1 | 7/2003 | White et al. |
| 6,616,695 | B1 | 9/2003 | Crozet et al. |
| 6,709,458 | B2 | 3/2004 | Michelson |
| 6,758,849 | B1 | 7/2004 | Michelson |
| 6,808,537 | B2 | 10/2004 | Michelson |
| 6,846,327 | B2 | 1/2005 | Khandkar et al. |
| 6,863,689 | B2 | 3/2005 | Ralph et al. |
| 6,923,810 | B1 | 8/2005 | Michelson |
| 6,962,606 | B2 | 11/2005 | Michelson |
| 6,997,953 | B2 | 2/2006 | Chung et al. |
| 7,141,068 | B2 | 11/2006 | Ross et al. |
| 7,153,325 | B2 | 12/2006 | Kim et al. |
| 7,186,267 | B2 | 3/2007 | Aston et al. |
| 7,341,601 | B2 | 3/2008 | Eisermann et al. |
| 7,410,501 | B2 | 8/2008 | Michelson |
| 7,429,270 | B2 | 9/2008 | Baumgartner et al. |
| 7,435,261 | B1 | 10/2008 | Castro |
| 7,452,369 | B2 | 11/2008 | Barry |
| 7,485,134 | B2 | 2/2009 | Simonson |
| 7,527,649 | B1 | 5/2009 | Blain |
| 7,537,616 | B1 | 5/2009 | Branch et al. |
| 7,621,952 | B2 | 11/2009 | Truckai et al. |
| 7,621,953 | B2 | 11/2009 | Braddock, Jr. et al. |
| 7,628,814 | B2 | 12/2009 | Studer et al. |
| 7,794,500 | B2 | 9/2010 | Felix |
| 7,799,056 | B2 | 9/2010 | Sankaran |
| 7,803,191 | B2 | 9/2010 | Biedermann et al. |
| 7,879,103 | B2 | 2/2011 | Gertzman |
| 7,935,149 | B2 | 5/2011 | Michelson |
| 8,016,887 | B1 | 9/2011 | Castro |
| 8,021,424 | B2 | 9/2011 | Beger et al. |
| 8,021,426 | B2 | 9/2011 | Segal et al. |
| 8,062,365 | B2 | 11/2011 | Schwab |
| 8,092,536 | B2 | 1/2012 | Ahrens et al. |
| 8,182,538 | B2 | 5/2012 | O'Neil et al. |
| 8,226,718 | B2 | 7/2012 | Castro |
| 8,241,363 | B2 | 8/2012 | Sommerich et al. |
| 8,246,683 | B2 | 8/2012 | Castro |
| 8,298,286 | B2 | 10/2012 | Trieu |
| 8,328,848 | B2 | 12/2012 | Lowery et al. |
| 8,361,149 | B2 | 1/2013 | Castro |
| 8,414,820 | B2 | 4/2013 | Bertele et al. |
| 8,430,930 | B2 | 4/2013 | Hunt |
| 8,435,300 | B2 | 5/2013 | Messerli et al. |
| 8,454,700 | B2 | 6/2013 | Lemoine et al. |
| 8,475,533 | B1 | 7/2013 | Castro |
| 8,551,173 | B2 | 10/2013 | Lechmann et al. |
| 8,556,978 | B2 | 10/2013 | Schaller |
| 8,613,769 | B2 | 12/2013 | Sears et al. |
| 8,623,090 | B2 | 1/2014 | Butler |
| 8,673,006 | B2 | 3/2014 | Castro |
| 8,709,042 | B2 | 4/2014 | Greenhalgh et al. |
| 8,740,981 | B2 | 6/2014 | Tornier et al. |
| 8,771,357 | B2 | 7/2014 | Biedermann et al. |
| 8,771,368 | B2 | 7/2014 | McKay |
| 8,795,362 | B2 | 8/2014 | Anderson et al. |
| 8,801,787 | B2 | 8/2014 | Schaller |
| 8,808,376 | B2 | 8/2014 | Schaller |
| 8,808,725 | B2 | 8/2014 | Altschuler et al. |
| 8,932,356 | B2 | 1/2015 | Kraus |
| 8,940,052 | B2 | 1/2015 | Lechmann et al. |
| 8,951,300 | B2 | 2/2015 | Parrish |
| 8,986,383 | B2 | 3/2015 | Castro |
| 9,039,766 | B1 | 5/2015 | Fonte |
| 9,173,746 | B2 | 11/2015 | Lowery et al. |
| 9,186,252 | B2 | 11/2015 | Leibinger |
| 9,186,257 | B2 | 11/2015 | Geisler et al. |
| 9,247,970 | B2 | 2/2016 | Teisen |
| 9,271,845 | B2 | 3/2016 | Hunt et al. |
| 9,295,562 | B2 | 3/2016 | Lechmann et al. |
| 9,402,733 | B1 | 8/2016 | To et al. |
| 9,408,651 | B2 | 8/2016 | Sennett et al. |
| 9,421,108 | B2 | 8/2016 | Hunt |
| 9,770,339 | B2 * | 9/2017 | Greenhalgh .......... A61F 2/4455 |
| 9,918,849 | B2 * | 3/2018 | Morris ................ A61F 2/30744 |
| 2001/0014826 | A1 | 8/2001 | Biedermann et al. |
| 2001/0032018 | A1 | 10/2001 | Castro et al. |
| 2002/0052656 | A1 | 5/2002 | Michelson |
| 2003/0078660 | A1 | 4/2003 | Clifford et al. |
| 2003/0083746 | A1 | 5/2003 | Kuslich |
| 2004/0193270 | A1 | 9/2004 | DiMauro et al. |
| 2004/0210312 | A1 | 10/2004 | Neumann |
| 2004/0225361 | A1 | 11/2004 | Glenn et al. |
| 2005/0177238 | A1 | 8/2005 | Khandkar et al. |
| 2005/0222681 | A1 | 10/2005 | Richley et al. |
| 2005/0278027 | A1 | 12/2005 | Hyde, Jr. |
| 2006/0041262 | A1 | 2/2006 | Calvert et al. |
| 2006/0052872 | A1 | 3/2006 | Studer et al. |
| 2006/0100706 | A1 | 5/2006 | Shadduck et al. |
| 2006/0147332 | A1 | 7/2006 | Jones et al. |
| 2006/0293753 | A1 | 12/2006 | Thramann |
| 2007/0027544 | A1 | 2/2007 | McCord et al. |
| 2007/0179610 | A1 | 8/2007 | Biedermann et al. |
| 2007/0198090 | A1 | 8/2007 | Abdou |
| 2007/0260324 | A1 | 11/2007 | Joshi et al. |
| 2008/0306595 | A1 | 12/2008 | McLeod et al. |
| 2008/0312742 | A1 | 12/2008 | Abernathie |
| 2009/0036985 | A1 | 2/2009 | Whiting |
| 2009/0048678 | A1 | 2/2009 | Saal et al. |
| 2009/0112321 | A1 | 4/2009 | Kitchen |
| 2009/0149958 | A1 | 6/2009 | Prewett et al. |
| 2009/0248162 | A1 | 10/2009 | Peckham |
| 2010/0286778 | A1 | 11/2010 | Eisermann et al. |
| 2011/0015741 | A1 | 1/2011 | Melkent et al. |
| 2011/0066192 | A1 | 3/2011 | Frasier et al. |
| 2011/0166660 | A1 | 7/2011 | Laurence |
| 2011/0190895 | A1 | 8/2011 | Segal et al. |
| 2011/0245926 | A1 | 10/2011 | Kitchen |
| 2011/0270401 | A1 | 11/2011 | McKay |
| 2011/0301709 | A1 | 12/2011 | Kraus et al. |
| 2011/0313532 | A1 | 12/2011 | Hunt |
| 2012/0191188 | A1 | 7/2012 | Huang |
| 2012/0191189 | A1 | 7/2012 | Huang |
| 2012/0296431 | A1 | 11/2012 | Kim et al. |
| 2013/0030529 | A1 | 1/2013 | Hunt et al. |

(56) References Cited

U.S. PATENT DOCUMENTS

| | | |
|---|---|---|
| 2013/0116793 A1 | 5/2013 | Kloss |
| 2013/0123935 A1 | 5/2013 | Hunt et al. |
| 2013/0158672 A1 | 6/2013 | Hunt |
| 2013/0184826 A1 | 7/2013 | Thaiyananthan |
| 2013/0190880 A1 | 7/2013 | Schaller |
| 2013/0218282 A1 | 8/2013 | Hunt |
| 2013/0218288 A1 | 8/2013 | Fonte et al. |
| 2013/0304211 A1 | 11/2013 | Trautwein et al. |
| 2014/0058513 A1 | 2/2014 | Gahman et al. |
| 2014/0121776 A1 | 5/2014 | Hunt |
| 2014/0142707 A1 | 5/2014 | Compton et al. |
| 2014/0195005 A1 | 7/2014 | McKay |
| 2014/0243980 A1 | 8/2014 | Sack et al. |
| 2014/0277457 A1 | 9/2014 | Yeung et al. |
| 2014/0277464 A1 | 9/2014 | Richter et al. |
| 2014/0277569 A1 | 9/2014 | Lange |
| 2014/0288649 A1 | 9/2014 | Hunt |
| 2014/0288650 A1 | 9/2014 | Hunt |
| 2014/0303745 A1 | 10/2014 | Anderson et al. |
| 2014/0309743 A1 | 10/2014 | Falahee |
| 2014/0358246 A1 | 12/2014 | Levy et al. |
| 2015/0127106 A1 | 5/2015 | Partee et al. |
| 2015/0282933 A1 | 10/2015 | Hunt |
| 2015/0282945 A1 | 10/2015 | Hunt |
| 2015/0282946 A1 | 10/2015 | Hunt |
| 2016/0045230 A1 | 2/2016 | Lowery et al. |
| 2016/0081809 A1 | 3/2016 | Schneider et al. |
| 2016/0193057 A1 | 7/2016 | Rhoda |
| 2016/0206439 A1 | 7/2016 | To et al. |
| 2016/0206440 A1 | 7/2016 | DeRidder et al. |
| 2016/0324656 A1 | 11/2016 | Morris et al. |
| 2017/0042697 A1 | 2/2017 | McShane, III et al. |
| 2017/0156879 A1* | 6/2017 | Janowski ................ A61F 2/447 |

FOREIGN PATENT DOCUMENTS

| | | |
|---|---|---|
| WO | 2011-159587 A1 | 12/2011 |
| WO | 2013-019543 A2 | 2/2013 |

OTHER PUBLICATIONS

International Search Report and Written Opinion dated May 25, 2018 for International Application No. PCT/US2018/22001.

* cited by examiner

IMPLANT WITH SUPPORTED HELICAL MEMBERS

BACKGROUND

The embodiments are generally directed to implants for supporting bone growth in a patient.

A variety of different implants are used in the body. Implants used in the body to stabilize an area and promote bone ingrowth provide both stability (i.e. minimal deformation under pressure over time) and space for bone ingrowth.

Spinal fusion, also known as spondylodesis or spondylosyndesis, is a surgical treatment method used for the treatment of various morbidities such as degenerative disc disease, spondylolisthesis (slippage of a vertebra), spinal stenosis, scoliosis, fracture, infection or tumor. The aim of the spinal fusion procedure is to reduce instability and thus pain.

In preparation for the spinal fusion, most of the intervertebral disc is removed. An implant, the spinal fusion cage, may be placed between the vertebra to maintain spine alignment and disc height. The fusion, i.e. bone bridge, occurs between the endplates of the vertebrae.

SUMMARY

In one aspect, aim implant includes a body defining a transverse plane dividing the implant into a superior half and an inferior half. The implant may also include a peripheral frame portion defining a periphery of the body and a central wall extending from a first side of the peripheral frame portion to a second side of the peripheral frame portion. The implant may further include a first bone contacting member attached to the body and disposed within the superior half of the implant. Also, the implant may include a first support member extending from a first point on a superior side of the peripheral frame portion to the first the bone contacting member and further extending inwardly of the bone contacting member into a central region of the implant and terminating at a second point on an inferior side of the peripheral frame portion adjacent to the first point from which the first support member extends.

In another aspect, an implant includes a body defined by a peripheral frame portion. The implant may also include a central wall extending from a first side of the peripheral frame portion to a second side of the peripheral frame portion; and a plurality of helical bone contacting members extending from the central wall of the body to the peripheral frame portion and defining outer surfaces of the implant. The implant may further include a first support member and a second support member that extend into the central region of the implant on a first side of the central wall. On the first side of the central wall, the peripheral frame portion, the central wall, and the plurality of helical bone contacting members define an inner volume in a central region of the implant. Also, the central region of the implant may be devoid of structural members except for the first support member and the second support member.

In another aspect, a method of fusing two vertebrae of a spinal column may include providing an implant, including a body defined by a peripheral frame portion and a central wall extending from a first side of the peripheral frame portion to a second side of the peripheral frame portion. The provided implant may further include a plurality of bone contacting members extending from the central wall of the body to the peripheral frame portion and defining outer surfaces of the implant; and a first support member and a second support member that extend into the central region of the implant on a first side of the central wall. On the first side of the central wall, the peripheral frame portion, the central wall, and the plurality of bone contacting members may define an inner volume in a central region of the implant. In addition, the central region of the implant may be devoid of structural members except for the first support member and the second support member. The method may include filling the inner volume of the implant with bone growth promoting material around the first support member and the second support member and inserting the implant between two vertebrae of a spinal column.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, with emphasis instead being placed upon illustrating the principles of the embodiments. Moreover, in the figures, like reference numerals designate corresponding parts throughout the different views.

DETAILED DESCRIPTION

The embodiments described herein are directed to an implant for use in a spine. The embodiments include implants with a body and one or more structural members.

In addition to the various provisions discussed below, any of the embodiments disclosed herein may make use of any of the body/support structures, frames, plates, coils or other structures disclosed in Morris et al., U.S. Publication Number 2016/0324656, published on Nov. 10, 2016, and titled "Coiled Implants and Systems and Methods of Use Thereof," which is incorporated herein by reference in its entirety. For purposes of convenience, the Morris application will be referred to throughout the present application as "The Coiled Implant Application."

Any of the embodiments disclosed herein may make use of any of the body/support structures, elements, frames, plates, or other structures disclosed in McShane III et al., U.S. Publication Number 2017/0042697, published on Feb. 16, 2017, and titled "Implant with Arched Bone Contacting Elements," which is hereby incorporated by reference in its entirety.

Also, any embodiments may make use of any of the body/support structures, elements, frames, plates or other structures disclosed in McShane III et al., U.S. Publication Number 2018/0110626, published on Apr. 26, 2018, and titled "Implant with Protected Fusion Zones," which is hereby incorporated by reference in its entirety and referred to as "The Protective Fusion Zones application."

Also, any embodiments may make use of any of the body/support structures, elements, frames, plates or other structures disclosed in McShane III et al., U.S. Publication Number 2018/0256351, published on Sep. 13, 2018, and titled "Implant with Structural Members Arranged Around a Ring," which is hereby incorporated by reference in its entirety and referred to as "The Ring application."

Figure 1:
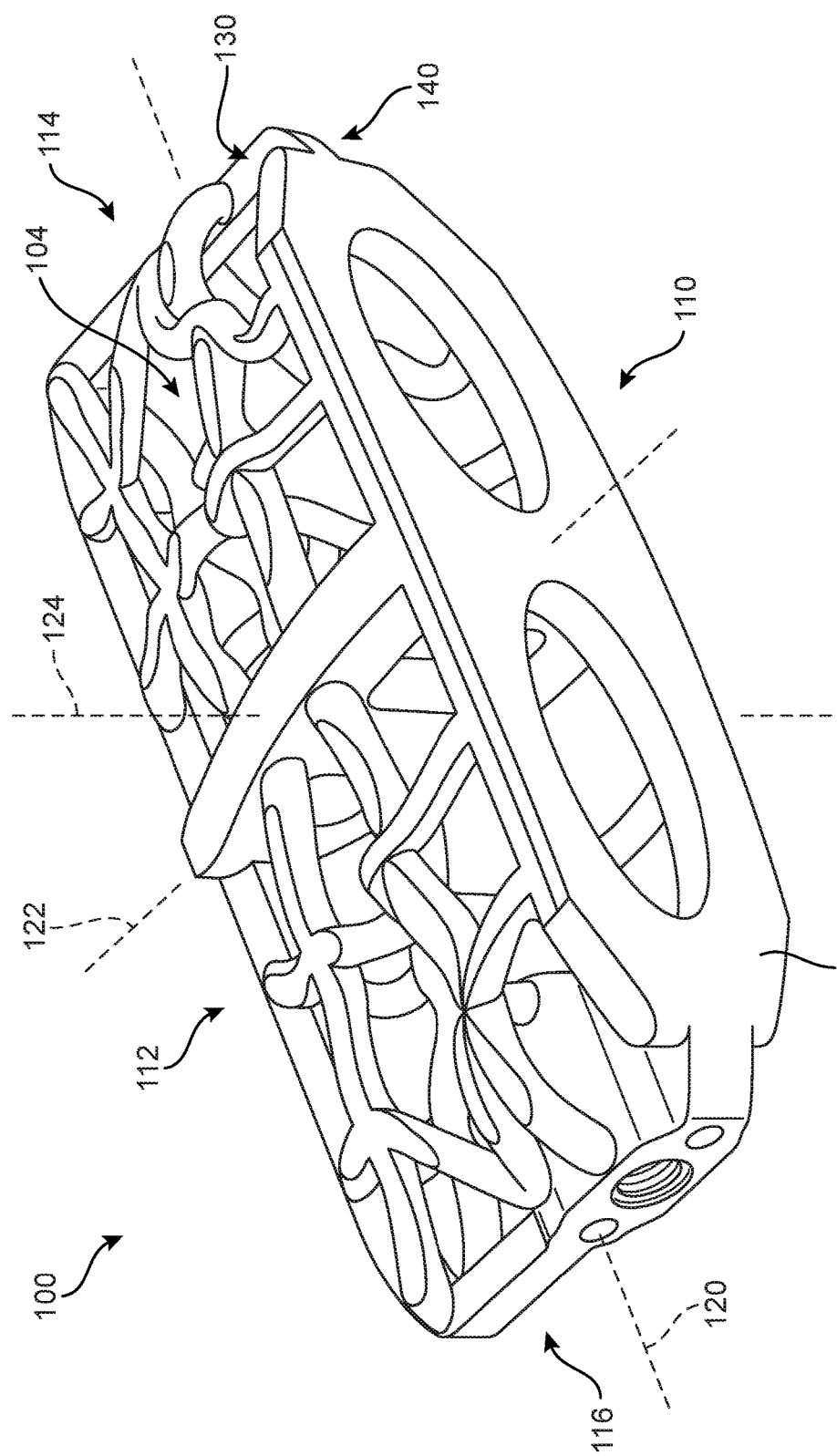
FIG. 1 is a schematic isometric superior view of an embodiment of an implant.
Figure 2:
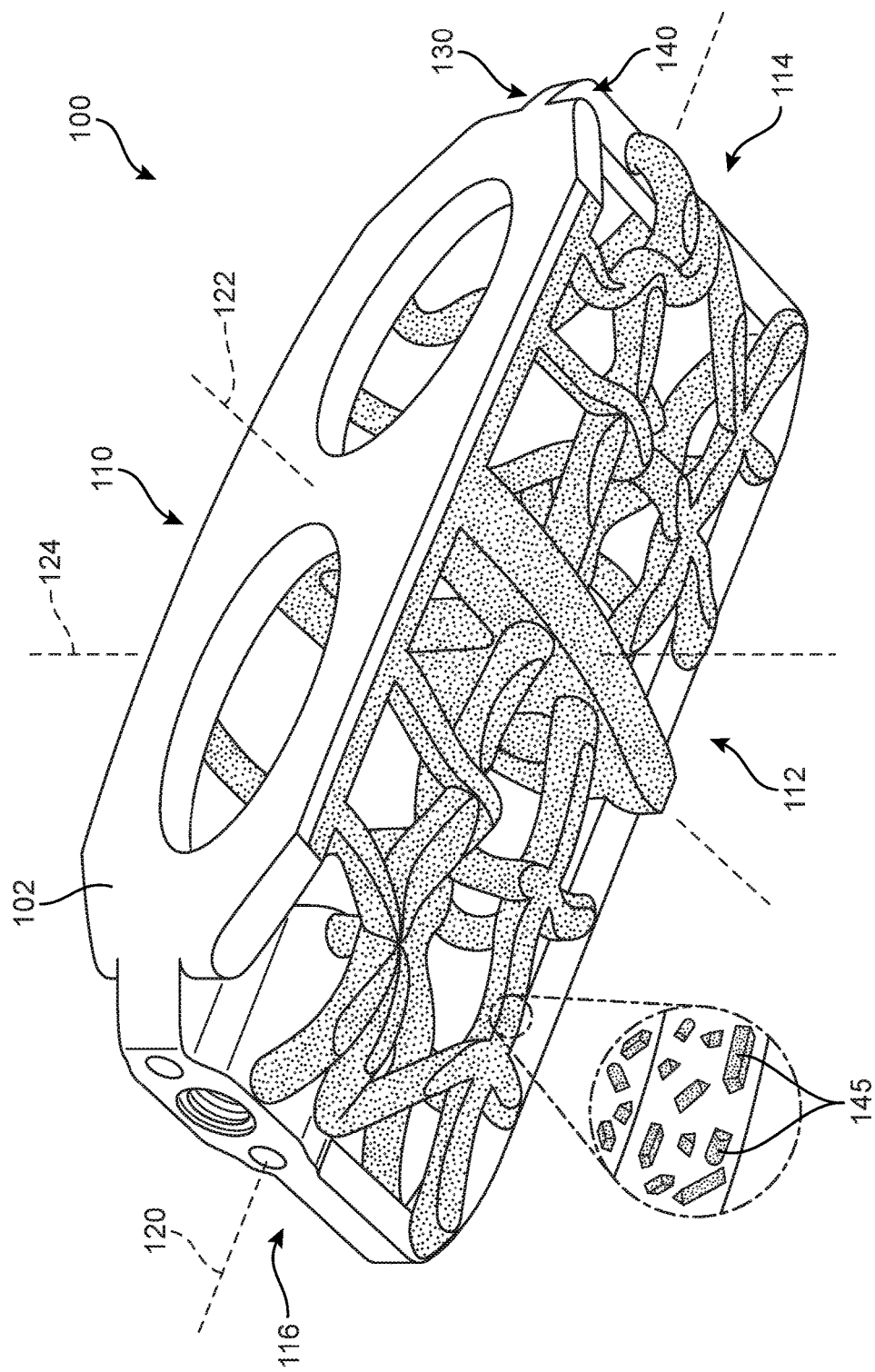
FIG. 2 is a schematic isometric inferior view of the implant of FIG. 1.

FIGS. 1 and 2 illustrate isometric views of an embodiment of an implant 100, which may be alternatively referred to as a device. Specifically, FIG. 1 is an isometric view of a top or superior side of implant 100, while FIG. 2 is an isometric view of a bottom or inferior side of implant 100. Implant 100 may also be referred to as a cage or fusion device. In some embodiments, implant 100 is configured to be implanted within a portion of the human body. In some embodiments, implant 100 may be configured for implantation into the spine. In some embodiments, implant 100 may be a spinal fusion implant, or spinal fusion device, that is inserted between adjacent vertebrae to provide support and/or facilitate fusion between the vertebrae.

In some embodiments, implant 100 may include a body 102. Body 102 may generally provide a frame or skeleton for implant 100. In some embodiments, implant 100 may also include a plurality of structural members 104. Plurality of structural members 104 may be fixedly attached to, and/or continuously formed (or "integrally formed") with, body 102. As used herein, the term "fixedly attached" shall refer to two components joined in a manner such that the components may not be readily separated (for example, without destroying one or both components).

As used herein, each structural member comprises a distinctive member or element that spans a portion of an implant. Structural members may overlap or intersect, similar to elements in a lattice or other 3D mesh structure. Some embodiments may use structural members in which the length of the member is greater than its width and its thickness. In embodiments where a structural member has an approximately circular cross-sectional shape, the structural member has a length greater than its diameter. In the embodiments seen in FIGS. 1-2, each structural member is seen to have an approximately rounded or circular cross-sectional shape (i.e., the member has the geometry of a solid tube). However, in other embodiments, a structural member could have any other cross-sectional shape, including, but not limited to, oval, various polygonal cross-sectional shapes, as well as any other regular and/or irregular cross-sectional shapes. In some cases, for example, the cross-sectional size and/or shape of a structural member could vary along its length (e.g., the diameter could change along its length).

For purposes of clarity, reference is made to various directional adjectives throughout the detailed description and in the claims. As used herein, the term "anterior" refers to a side or portion of an implant that is intended to be oriented towards the front of the human body when the implant has been placed in the body. Likewise, the term "posterior" refers to a side or portion of an implant that is intended to be oriented towards the back of the human body following implantation. In addition, the term "superior" refers to a side or portion of an implant that is intended to be oriented towards a top (e.g., the head) of the body while "inferior" refers to a side or portion of an implant that is intended to be oriented towards a bottom of the body. Reference is also made herein to "lateral" sides or portions of an implant, which are sides, or portions, facing along a lateral direction of the body (which correspond with the left or right sides of a patient).

In FIGS. 1-2, implant 100 is understood to be configured with an anterior side 110 and a posterior side 112. Implant 100 may also include a first lateral side 114 and a second lateral side 116 that extend between the posterior side 112 and the anterior side 110 on opposing sides of implant 100. Furthermore, implant 100 may also include a superior side 130 and an inferior side 140.

Reference is also made to directions or axes that are relative to the implant itself, rather than to its intended orientation with regards to the body. For example, the term "distal" refers to a part that is located further from a center of an implant, while the term "proximal" refers to a part that is located closer to the center of the implant. As used herein, the "center of the implant" could be the center of mass and/or a central plane and/or another centrally located reference surface.

An implant may also be associated with various axes. Referring to FIG. 1, implant 100 may be associated with a longitudinal axis 120 that extends along the longest dimension of implant 100 between first lateral side 114 and second lateral side 116. Additionally, implant 100 may be associated with a posterior-anterior axis 122 (also referred to as a "widthwise axis") that extends along the widthwise dimension of implant 100, between posterior side 112 and anterior side 110. Moreover, implant 100 may be associated with a vertical axis 124 that extends along the thickness dimension of implant 100 and which is generally perpendicular to both longitudinal axis 120 and posterior-anterior axis 122.

An implant may also be associated with various reference planes or surfaces. As used herein, the term "median plane" refers to a vertical plane which passes from the anterior side to the posterior side of the implant, dividing the implant into right and left halves, or lateral halves. As used herein, the term "transverse plane" refers to a horizontal plane located in the center of the implant that divides the implant into superior and inferior halves. As used herein, the term "coronal plane" refers to a vertical plane located in the center of the implant that divides the implant into anterior and posterior halves. In some embodiments, the implant is symmetric about two planes, such as the median and the transverse plane.

Embodiments can include provisions for texturing one or more surfaces of an implant. Such texturing can increase or otherwise promote bone growth and/or fusion to surfaces of the implant. In some embodiments, bone contacting members may be textured while support members may not be textured. This helps initial bone growth to be directed along the bone contacting members, rather than growing initially across support members. In other embodiments, however, support members could include surface texturing. In still further embodiments, one or more surfaces of a body could include surface texturing.

In some embodiments, the surface structure of one or more regions of an implant may be roughened or provided with irregularities. Generally, this roughened structure may be accomplished through the use of acid etching, bead or grit blasting, sputter coating with titanium, sintering beads of titanium or cobalt chrome onto the implant surface, as well as other methods. In some embodiments, the roughness can be created by 3D printing a raised pattern on the surface of one or more regions of an implant. In some embodiments, the resulting roughened surface may have pores of varying sizes. In some embodiments, pore sizes could range between approximately 0.2 mm and 0.8 mm. In one embodiment, pore sizes could be approximately 0.5 mm. In other embodiments, surface roughness comprising pore sizes less than 0.2 mm and/or greater than 0.8 mm are possible. The embodiments can make use of the surface texturing parts, features, processes or methods as disclosed in The Protected Fusion Zone Application.

As shown in FIG. 2, in some embodiments, various portions of implant 100 may include textured surfaces. For example, as illustrated in the enlarged portion of FIG. 2, texture may be provided by attaching or otherwise forming portions of implant 100 with three dimensional geometric elements 145. Three dimensional geometric elements 145 may have any suitable size, shape, and distribution, as discussed above.

Figure 3:
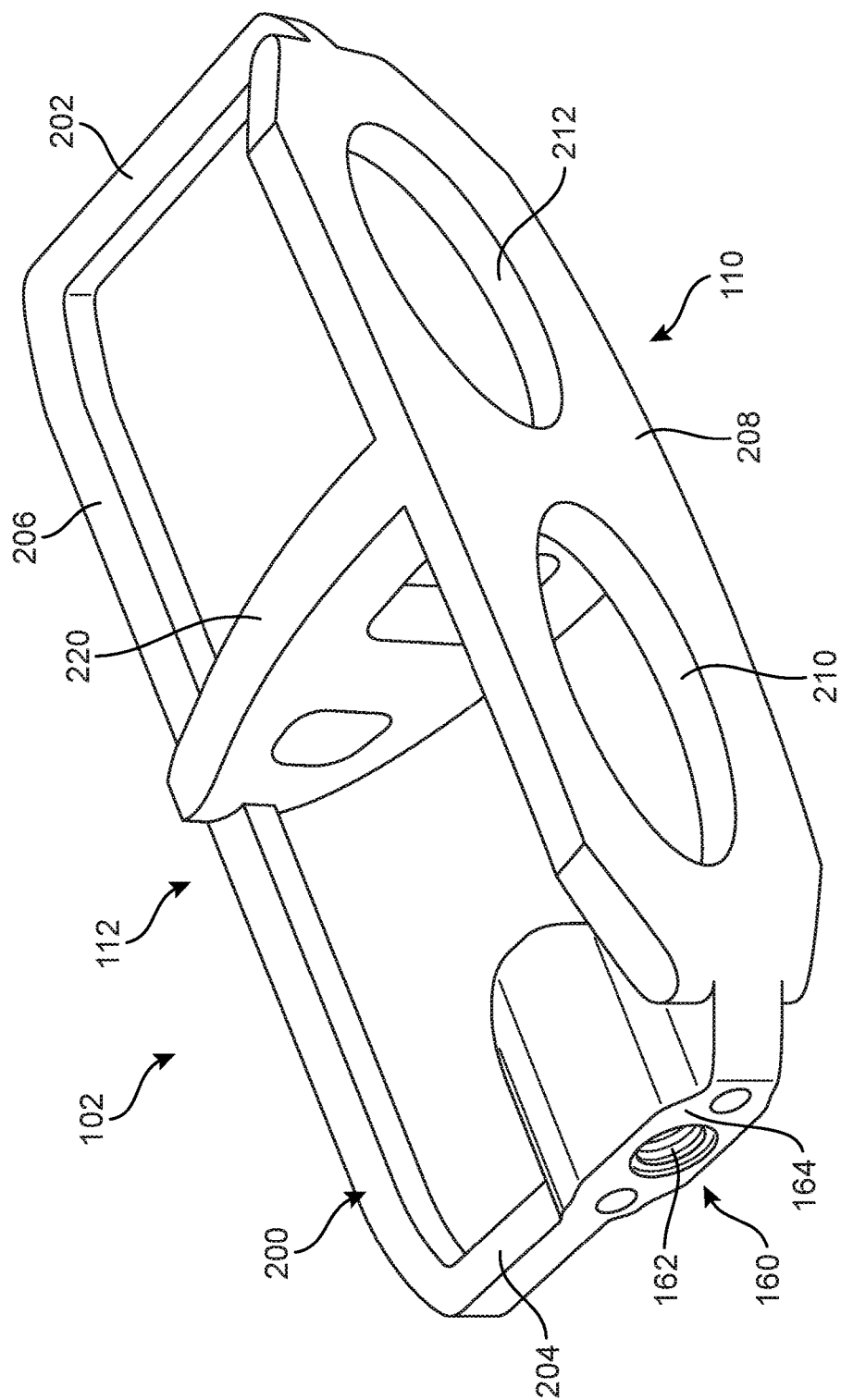
FIG. 3 is a schematic isometric superior view of a peripheral frame portion of the implant of FIG. 1 shown in isolation.

FIG. 3 illustrates a schematic isometric view of body 102 in isolation, with plurality of structural members 104 removed for purposes of clarity. In some embodiments, a body could include distinct frame portions that are oriented in different directions. In the embodiment shown in FIG. 3, body 102 includes a peripheral frame portion 200, also referred to as simply "peripheral portion 200". In some embodiments, peripheral portion 200 has a longest dimension aligned with longitudinal axis 120 and a widthwise dimension (e.g., the second longest dimension) aligned with posterior-anterior axis 122 of implant 100 (see FIGS. 1 and 2). Peripheral frame portion 200 comprises a first lateral frame portion 202, a second lateral frame portion 204 and a posterior frame portion 206, which primarily lie in the transverse plane.

In some embodiments, one or more sides of an implant (including lateral sides and/or anterior/posterior sides) could include a vertically oriented peripheral frame portion. In the embodiment of FIG. 3, body 102 is seen to include a vertically oriented peripheral frame portion 208 disposed at anterior side 110, which may also be referred to as an "anterior wall" of implant 100. In contrast, posterior side 112 lacks any frame portion or wall that extends vertically beyond the thickness of peripheral portion 200 in the embodiments of FIGS. 3-4. The presence of vertically oriented peripheral frame portion 208 may improve support and strength against vertical loads applied along the anterior side of the spine.

Although the present embodiment uses a vertically oriented frame or wall on the anterior side of implant 100, in other embodiments, a vertically oriented frame or wall could be located on the posterior side of implant 100 and/or on a lateral side of implant 100. In still other embodiments, the implant may lack any vertical walls along its perimeter (i.e., along the posterior, anterior or lateral sides).

As shown in FIG. 3, body 102 of implant 100 may include a central wall 220 which extends between vertically oriented peripheral frame portion 208 and posterior frame portion 206.

Figure 4:
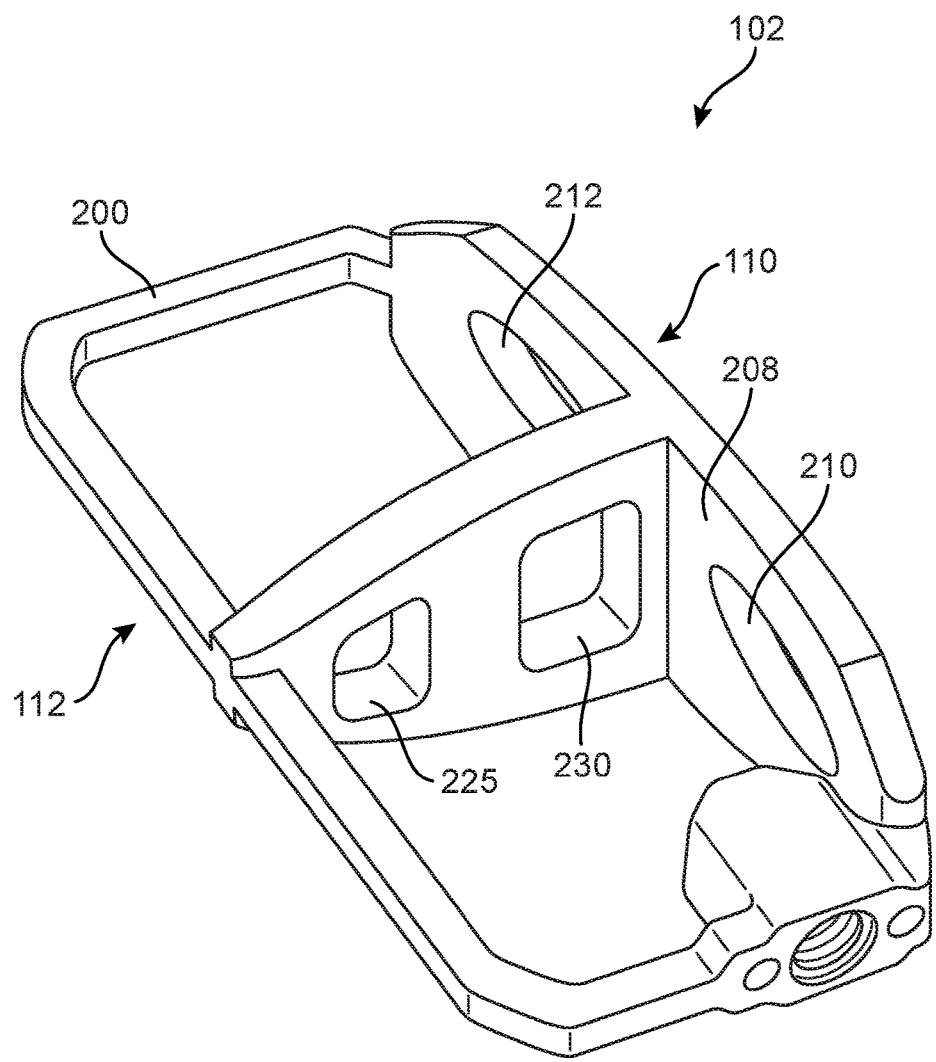
FIG. 4 is a schematic perspective lateral view of the peripheral frame portion of the implant of FIG. 1 shown in isolation.

FIG. 4 is a schematic perspective lateral view of an embodiment of implant 100. In some embodiments, vertically oriented peripheral frame portion 208 could include openings. In other embodiments, vertically oriented peripheral frame portion 208 may not include openings. In some embodiments, openings in a frame portion could provide an access point for inserting bone graft material or BGPM into an interior of an implant. The number, size and/or shape of openings in vertically oriented peripheral frame portion 208 could vary. In some cases, three or more openings could be used. In other cases, two openings could be used. In still other cases, a single opening could be used. Exemplary shapes for openings that could be used include, but are not limited to, rounded openings, rectangular openings, polygonal openings, regular openings and/or irregular openings. In the embodiment of FIGS. 3-4, vertically oriented peripheral frame portion 208 includes two large oval-shaped windows that may facilitate insertion of bone graft material (or BGMP) into an interior of the implant. Specifically, vertically oriented peripheral frame portion 208 includes first window 210 and second window 212.

Some embodiments can include provisions that facilitate implantation, including insertion and/or fixation of the implant. Some embodiments can include a fastener receiving portion. For example, as shown in FIG. 3, implant 100 may include a fastener receiving portion 160. Fastener receiving portion 160 includes a threaded opening 162 and a reinforced collar 164 to support threaded opening 162. In some embodiments, threaded opening 162 may be configured to receive a tool with a corresponding threaded tip to facilitate implantation of implant 100. In some embodiments, threaded opening 162 may be used with a screw to help attach implant 100 to a bone or another fixation device. In other embodiments, any other features for receiving fasteners and/or implantation tools could be incorporated into implant 100.

In some embodiments, an implant can be configured with one or more symmetries. In some cases, an implant may have a mirrored symmetry about one or more reference planes.

In some embodiments, 100 may include at least one axis of mirror symmetry. For purposes of reference, implant 100 may be split into a superior half and an inferior half. Here, the "superior half" of implant 100 includes the portions of body 102 and plurality of structural members 104 disposed above the transverse plane. Likewise, the "inferior half" of implant 100 includes the portions of body 102 and plurality of structural members 104 disposed below the transverse.

With respect to the transverse plane (which coincides generally with the plane defined by first lateral frame portion 202, second lateral frame portion 204 and posterior frame portion 206), it may be seen that the superior half of implant 100 mirrors the inferior half of implant 100, at least approximately. In some embodiments, this may include not only the geometry of the body but also the shape, size, and orientations of each structural member.

Moreover, with respect to the median plane (which approximately divides implant 100 into two lateral halves), it may be seen that two lateral halves mirror one another approximately on either side of center wall 220. This includes not only the geometry of the body but also the shape, size and orientations of each structural member.

In some embodiments, central wall 220 may include one or more structural features configured to house bone ingrowth promoting material. For example, as shown in FIG. 4, in some embodiments, central wall 220 may include one or more thru-holes, such as a first thru-hole 225 and a second thru-hole 230.

An implant may include two or more kinds of structural members (or structural elements). In some embodiments, an implant can include one or more bone contacting structural members, or simply "bone contacting members." Bone contacting members may generally be substantially fully exposed on the outer surfaces of an implant, including along the superior and inferior sides of the implant. Thus, bone contacting members may be alternatively referred to as "outer members."

Figure 5:
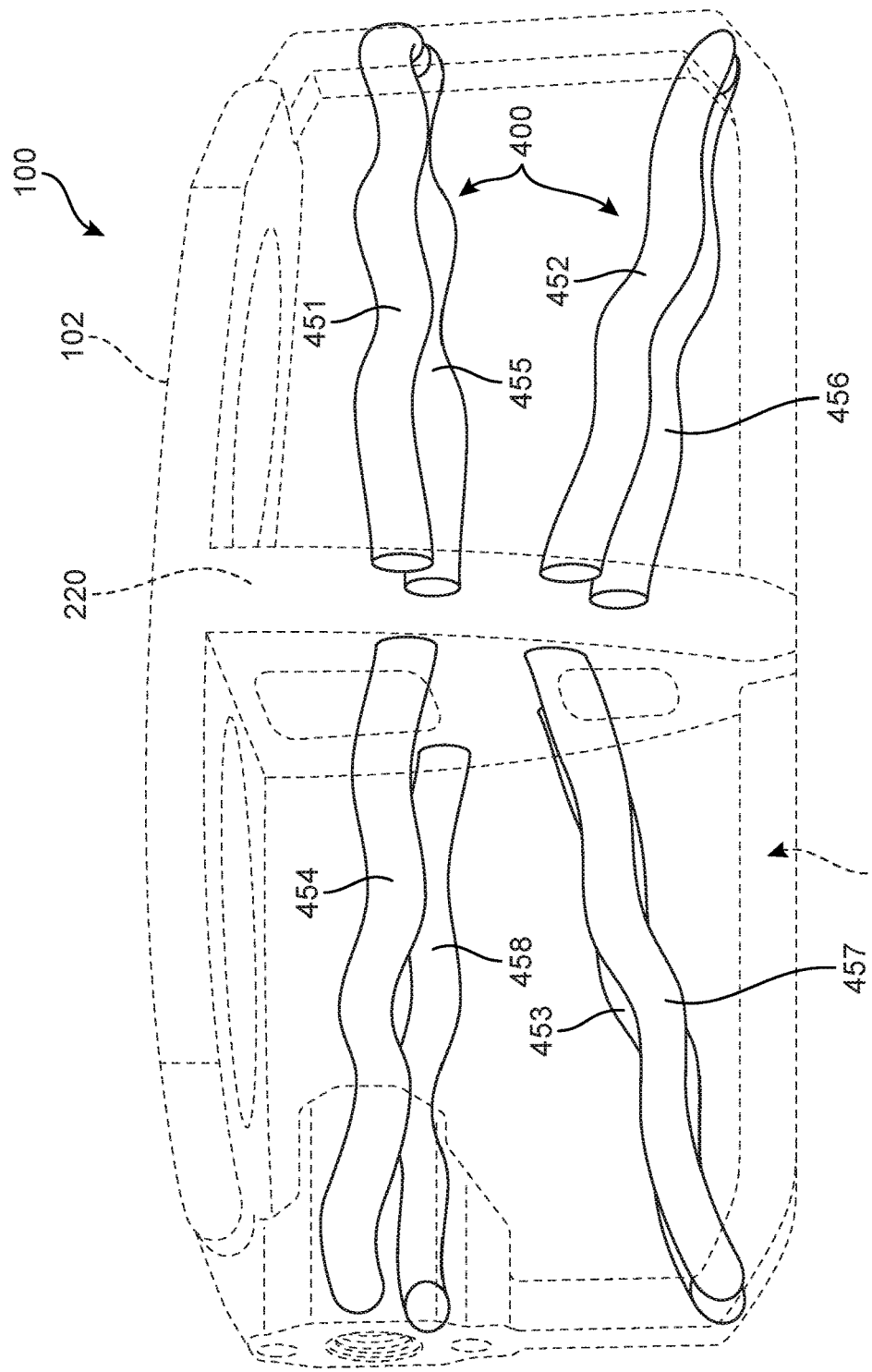
FIG. 5 is a schematic perspective view of helical bone contacting members of the implant of FIG. 1 with the peripheral frame portion shown in phantom.

FIG. 5 is a schematic perspective view of helical bone contacting members of the implant of FIG. 1 with peripheral frame portion 200 shown in phantom. As shown in FIG. 5, implant 100 may include a plurality of bone contacting members 400 attached to body 102. For example, bone contacting members 400 may include a first bone contacting member 451 attached to central wall 220 and extending to peripheral frame portion 200. As also shown in FIG. 5, implant 100 may include a second bone contacting member 452, a third bone contacting member 453, and a fourth bone contacting member 454, all of which may be disposed on the inferior half of implant 100. Similarly, implant 100 may also include a first bone contacting member 455, a second bone contacting member 456, a third bone contacting member 457, and a fourth bone contacting member 458, all of which may be disposed on the superior half of implant 100. As shown in FIG. 5, the arrangement of bone contacting members 400 may be generally symmetrical about central wall 220, as well as in the anterior-posterior direction. However, in some embodiments, bone contacting members 400 may be arranged in non-symmetrical configurations.

Embodiments may include provisions to minimize the number of bars or other supports needed, thereby increasing the interior volume available to receive new bone growth. In some embodiments, central wall 220 may have a larger thickness to provide reinforcement. For example, as shown in FIG. 5, central wall 220 may have a thickness that is greater than the thickness of the bone contacting members 400.

Helical Geometry of Outer Members

Embodiments can include provisions for protecting bone growth along and adjacent to bone contacting members of an implant. In some embodiments, a bone contacting member can be configured with a geometry that helps to protect new bone growth in selected regions or "protected fusion zones." In some embodiments, a bone contacting member can have a spiral, helical or twisted geometry that provide a series of such protected fusion zones for enhanced bone growth.

Some outer members may have a generalized helical geometry. As used herein, a "generalized helical geometry" or "spiraling geometry" refers to a geometry where a part (portion, member, etc.) winds, turns, twists, rotates or is otherwise curved around a fixed path. In some cases, the fixed path could be straight. In other cases, the fixed path can be curved. In the present embodiments, for example, the fixed path is generally a combination of straight segments and curved segments.

Figure 6:
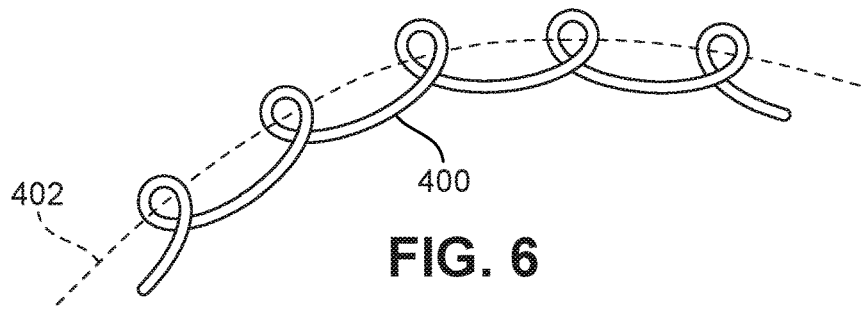
FIG. 6 is a schematic view of a curve with a generalized helical geometry, according to an embodiment.

FIG. 6 illustrates a schematic view of a curve 400 with a generalized helical geometry. Curve 400 is seen to wind around a fixed path 402 that is itself curved. In contrast to curve 400, however, fixed path 402 does not include any turns, windings, etc. An example of a helical curve with a straight fixed path is shown in FIG. 1 of the Coiled Implant Application.

Curves having a generalized helical geometry (also referred to as generalized helical curves) may be characterized by "coils," "turns," or "windings" about a fixed path. Exemplary parameters that may characterize the specific geometry of a generalized helical curve can include coil diameter (including both a major and minor diameter) and the pitch (i.e., spacing between adjacent coils). In some cases, the "amplitude" of a coil or loop may also be used to describe the diameter or widthwise dimension of the coil or loop. Each of these parameters could be constant or could vary over the length of a generalized helical curve.

Figure 7:
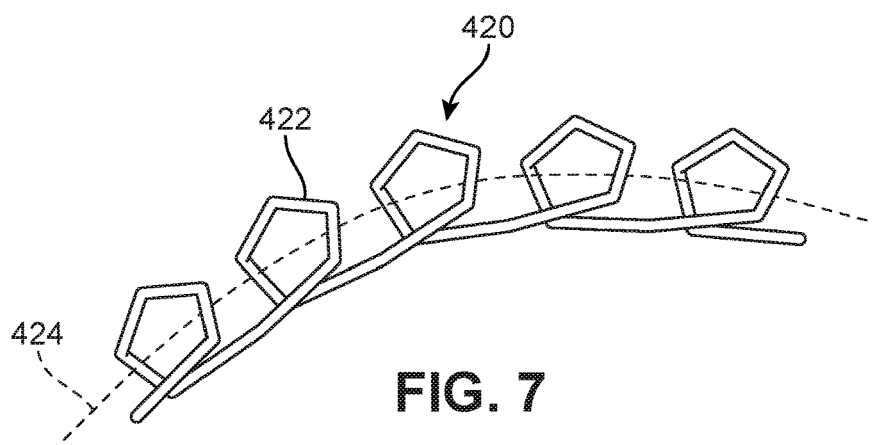
FIG. 7 is a schematic view of another curve with a generalized helical geometry, according to an embodiment.

Generalized helical curves need not be circular or even round. In some embodiments, for example, a generalized helical curve could have linearly-segmented shape (or locally polygonal shape) such that each "coil" or "turn" is comprised of straight line segments rather than arcs or other curved segments. An example of such a generalized helical curve is shown in FIG. 7. Referring to FIG. 7, generalized helical curve 420 is seen to be comprised of straight-line segments 422. The angles between adjacent segments are such that they wind or loop around a fixed path 424 in "polygonal coils".

Figure 8:
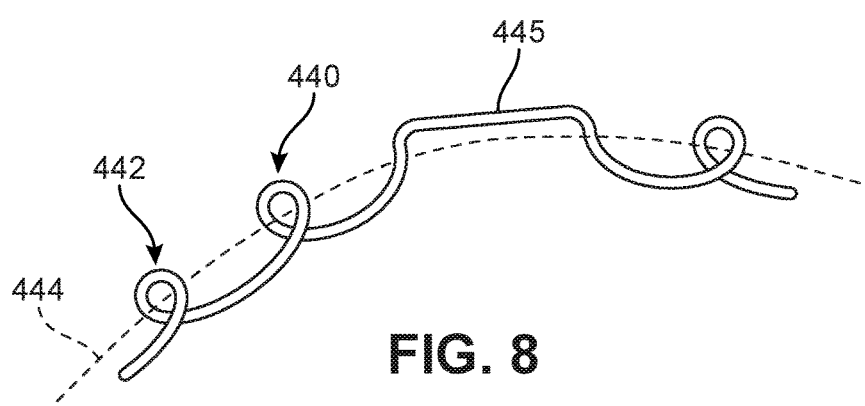
FIG. 8 is a schematic view of a curve with a generalized helical geometry including a straight segment, according to an embodiment.

Generalized helical curves may also include combinations of curved and straight segments. An example of such a combination curve is depicted in FIG. 8. Referring to FIG. 8, generalized helical curve 440 includes generally round (i.e., curved) coil segments 442 curing around a fixed path 444. In addition, curve 440 includes at least one straight-line segment that extends between adjacent coils.

Although the generalized curves shown in FIGS. 6-8 are one-dimensional curves, similar principles may be applied to three-dimensional parts, including structural members.

For purposes of characterizing the geometry of one or more structural members, each structural member can be understood to have a "central member curve." The central member curve of each structural member may be defined as a curve that extends along the length of the structural member such that each point along the curve is centrally positioned within the structural member.

In embodiments where a structural member winds or loops around a fixed path with an amplitude or diameter that is much greater than the cross-sectional diameter of the structural member itself, the structural member may be wound into visible distinct coils. Such coils are discussed in thorough detail in the Coiled Implant Application. In other embodiments, however, a structural member could be wound around a fixed path with an amplitude or diameter that is less than the cross-sectional diameter of the structural member itself. In such a case the resulting geometry of a structural member may appear to be twisted, but the geometry may lack the distinct coils seen in the Coiled Implant Application. However, it may be appreciated that while the outermost surface of such a structural member may not exhibit distinct coils, the central member curve of the structural member does have such coils or turns and moreover has a clear generalized helical geometry.

Figure 9:
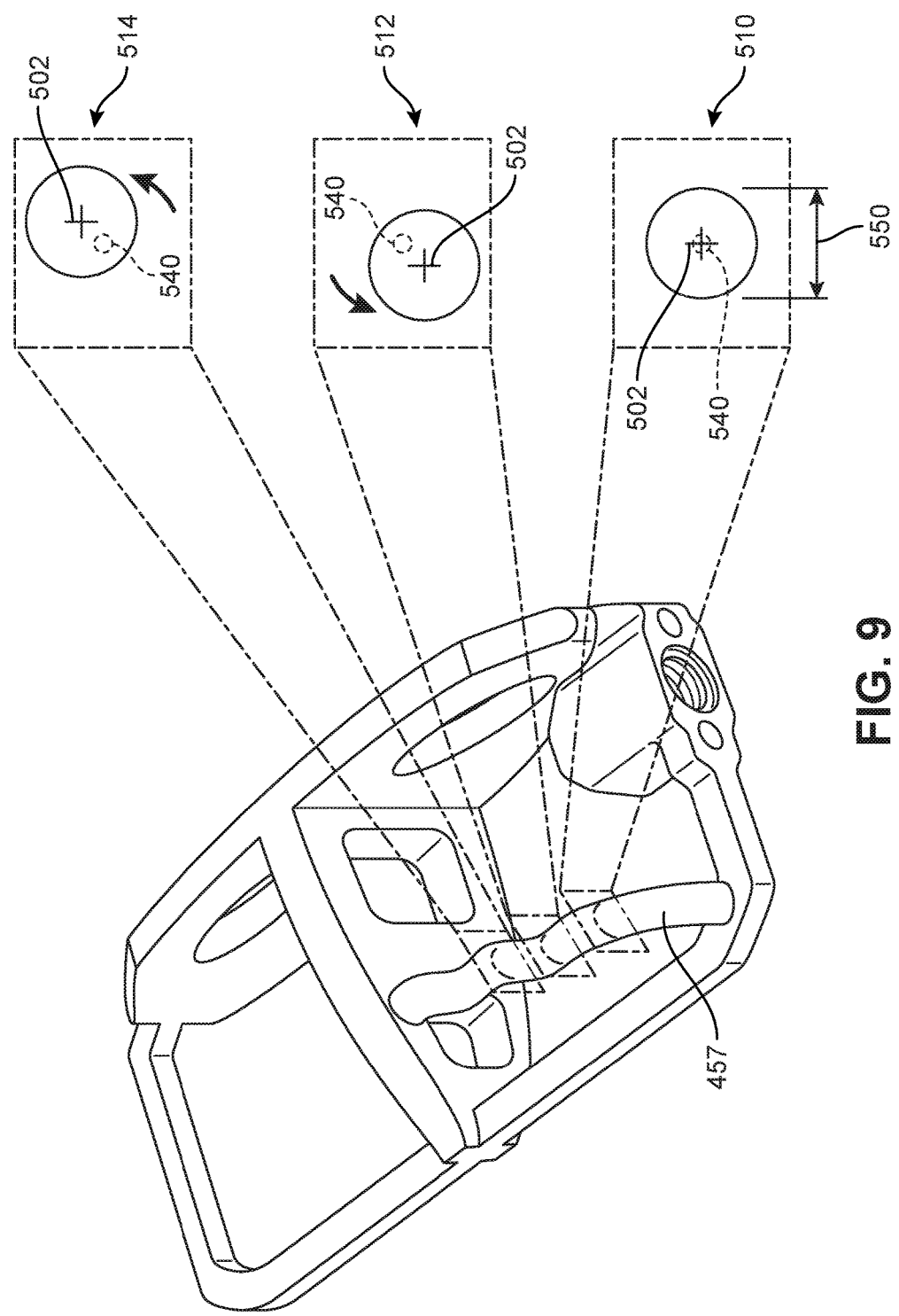
FIG. 9 is a schematic lateral perspective view of a portion of an implant with a helical bone contacting member shown in isolation so as to demonstrate the generalized helical geometry of the helical bone contacting member, according to an embodiment.
Figure 10:
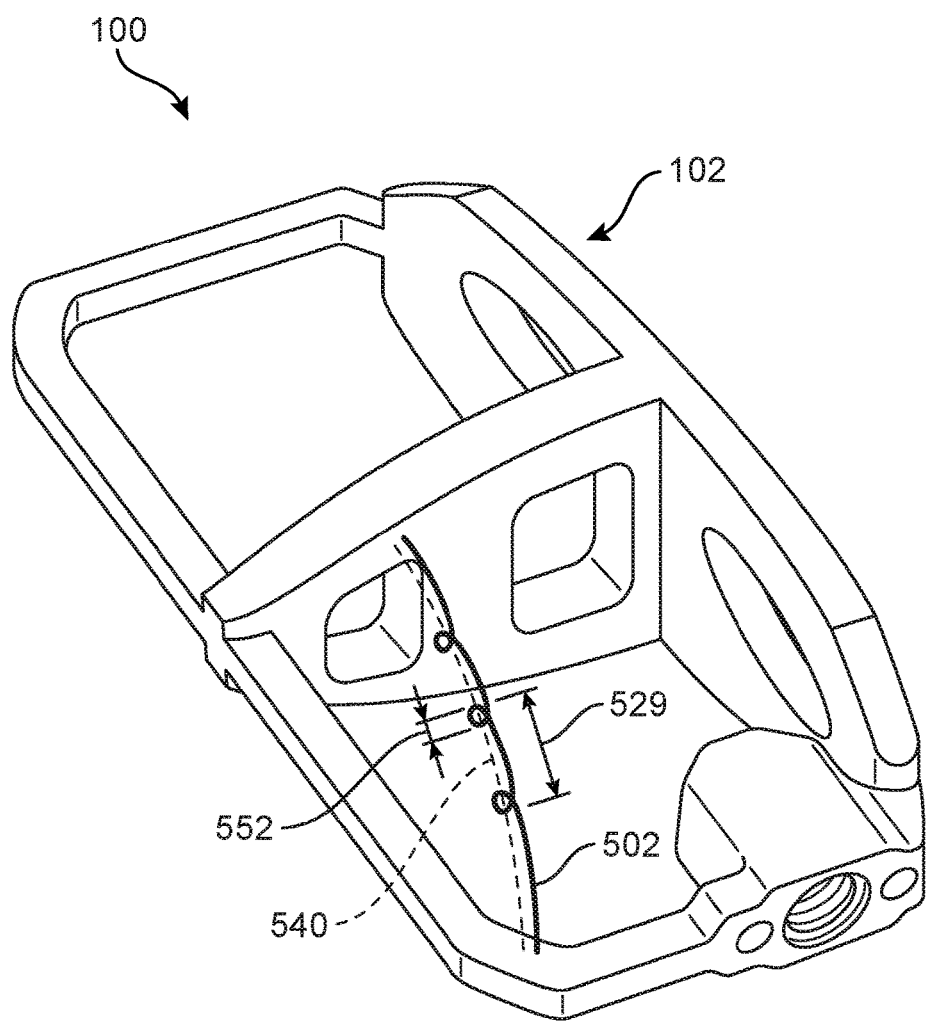
FIG. 10 is a schematic lateral perspective view of the implant of FIG. 1, including the central member curves of the structural members seen in FIG. 9.

FIG. 9 is a schematic perspective view of a portion of an implant with a helical bone contacting member shown in isolation so as to demonstrate the generalized helical geometry of the helical bone contacting member, according to an embodiment. FIG. 9 illustrates implant 100 with a single bone contacting member 457 shown. The other structural members have been removed from FIG. 9 for purposes of clarity. FIG. 10 is a schematic perspective view of body 102 with all structural members removed for clarity.

As seen in FIG. 9, the outer surface of bone contacting member 457 exhibits a twisted geometry indicative of a spiral or helix. However, since the winding occurs with an amplitude much smaller than the thickness of bone contacting member 457, the geometry of the part may be difficult to discern. The generalized helical geometry of bone contacting member 457 becomes much clearer when the geometry of its central member curve 502 (which is clearly seen in FIG. 10) is considered as it winds around a fixed path 540 (also shown in FIG. 10).

For purposes of illustrating the winding geometry of bone contacting member 457, FIG. 9 includes a sequence of cross-sectional views taken along outer member 300. In a first cross-sectional view of a first portion 510, a first point (indicated using a cross in FIG. 9) of central member curve 502 is seen to be approximately aligned with a corresponding point (indicated using a circle) of fixed path 540. At a second portion 512, a second point of central member curve 502 is seen to be positioned at a first rotational position away from a corresponding point of fixed path 540. At a third portion 514, a third point of central member curve 502 is seen to be positioned at a second rotational position from a corresponding of fixed path 540. Thus, it can be seen that as bone contacting member 457 twists with a small amplitude along its extension between base portion 200 and central keel portion 202, central member curve 502 indeed winds or spirals around fixed path 540. Here, it may be understood that fixed path 540 represents the "average" or approximate path of bone contacting member 457 that ignores the helical deviations at some segments.

As clearly seen in comparing FIGS. 9 and 10, the cross-sectional diameter 550 of bone contacting member 457 is greater than a corresponding winding diameter 552 of the coils or turns in central member curve 502. In other embodiments, the cross-sectional diameter of a bone contacting member could be less than a corresponding winding diameter of the coils or turns of its central member curve. In such an embodiment, the outer member would be configured in a series of distinct coils.

Referring to FIGS. 9 and 10, bone contacting member 457 does not have a generalized helical geometry through its entire length. Instead, its central member curve is configured with a winding segment where the central member curve completes several full turns (three in FIGS. 9-10) around a fixed path. Away from the winding segment, its central member curve may not include any turns, twists, etc.

Although the present embodiment includes at least one outer member with a winding segment that makes one or more full turns around a fixed path, other embodiments could be configured with central member curves that only make partial turns around a fixed path.

While the description here has focused on the geometry of a single bone contacting member 457, it may be appreciated that some or all of the remaining outer members in plurality of structural members 104 may have a similar generalized helical geometry. It may be further appreciated that two different bone contacting members could have slightly different geometries, with distinct bone contacting member curves that include variations in the number of windings, shape of the windings, etc.

In some embodiments, an implant can include bone contacting members that are locally helical over small distances compared to the length, width or height of the implant. For example, implant 100 may be characterized as having bone contacting members that are locally helical or locally spiraling, rather than globally helical. In particular, each bone contacting members of implant 100 is bounded within a single quadrant of implant 100 and does not cross the transverse plane or the median plane of implant 100. Thus, a full turn of the outer members is accomplished over distances that are much smaller than half the length, width or height of the implant. This allows multiple windings within each quadrant of the implant and also results in the pitch between windings being smaller than the length, width or height of the implant. For example, in FIG. 10, central member curve 502 has a pitch 529 between adjacent windings or turns that is less than one third of the length of bone contacting member 457. Pitch 529 is also less than one tenth of the length of implant 100. This relatively small pitch size allows for a greater number of proximal surface regions along each bone contacting member, thereby increasing the number of bone contacting surfaces of the inferior and superior surfaces of implant 100.

In some embodiments, an implant can include one or more structural members that provide support to one or more bone contacting members. Such supporting structural members may be referred to as "support members." In some embodiments, at least some portions of each support member may be generally disposed inwardly of the bone contacting members.

Figure 11:
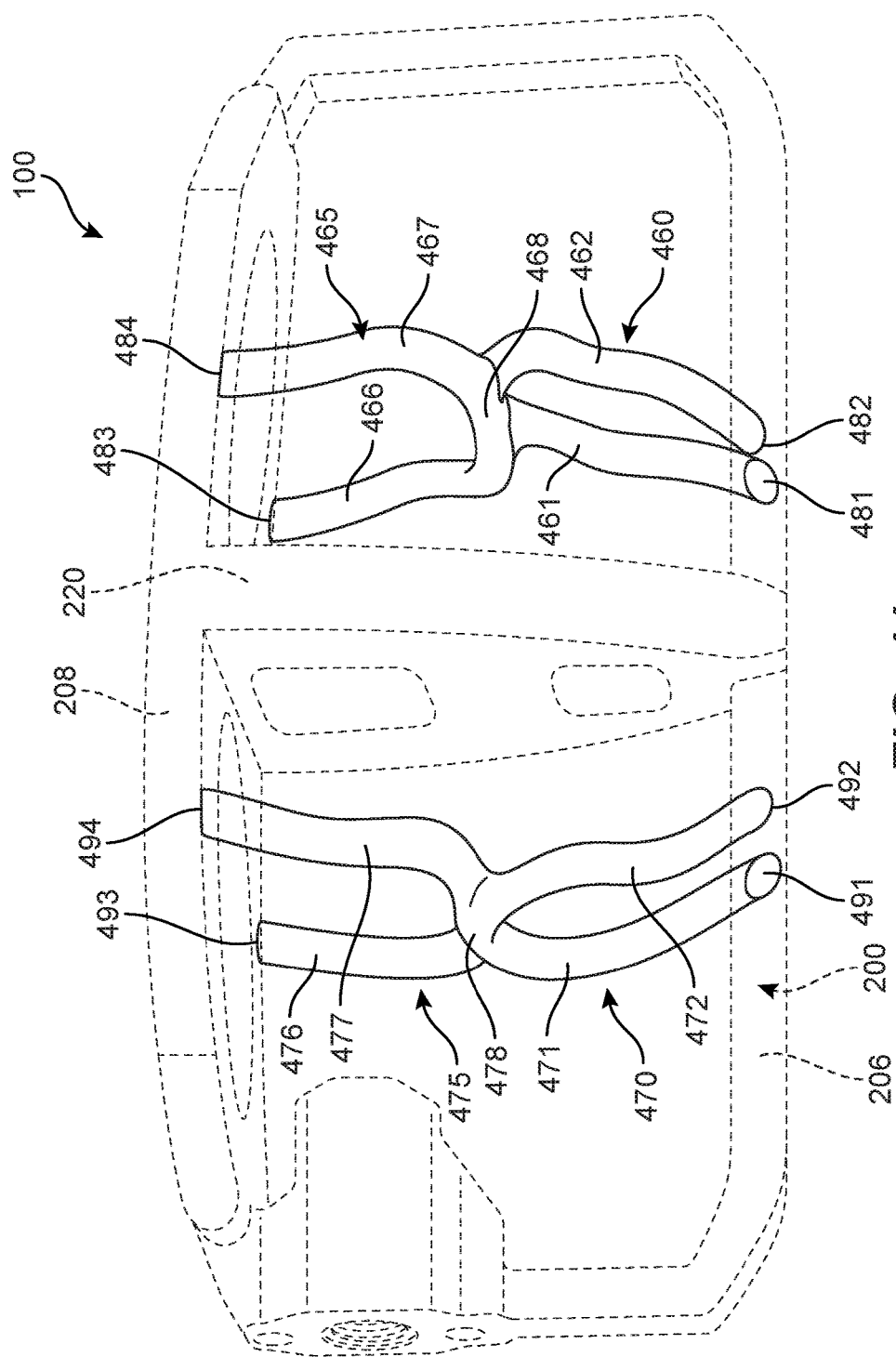
FIG. 11 is a schematic perspective view of a plurality of support members arranged within the body of the implant of FIG. 1, with the peripheral frame portion shown in phantom.

FIG. 11 is a schematic perspective view of a plurality of support members arranged within the body of implant 100, with peripheral frame portion 200 shown in phantom. As shown in FIG. 11, implant 100 may include a first support member 460, including a first leg 461 extending from a first point 481 on a superior side of peripheral frame portion 200 to a bone contacting member (see FIG. 13) and further extending inwardly of the bone contacting member into a central region of the implant and extending down a second leg 462 terminating at a second point 482 on an inferior side of peripheral frame portion 200 adjacent to first point 481 from which first support member 460 extends.

As further shown in FIG. 11, implant 100 may include a second support member 465 extending from a third point 483 on peripheral frame portion 200 opposite first point 481 along a first leg 466 to a bone contacting member (see FIG. 13) and further extending inwardly of the bone contacting members and extending along a second leg 467 and terminating at a fourth point 484 on peripheral frame portion 200. As shown in FIG. 11, in some embodiments, first point 481 and second point 482 on peripheral frame portion 200 may be disposed on the first side of implant 100 and third point 483 and fourth point 484 may be disposed on the second side of implant 100.

In some embodiments, the support members may be substantially U-shaped. For example, as shown in FIG. 11, first support member 460 and second support member 465 may be substantially U-shaped. Also, in some embodiments, the support members may be connected to one another. For example, as shown in FIG. 11, first support member 460 and second support member 465 may be connected to one another at the bottoms of the two U-shapes, in an overlapping region 468 in the central region of the implant inward of the bone contacting members.

In some embodiments, at least one of first support member 460 and second support member 465 may include one or more bone contacting portions. For example, as shown in FIG. 11, legs 461, 462, 466, and 467 of first support member 460 and second support member 465 may be exposed to the outside of implant 100, and thus, may include bone contacting portions.

As shown in FIG. 11, implant 100 may include a third support member 470, including a first leg 471 extending from a first point 491 on a superior side of peripheral frame portion 200 to a bone contacting member (see FIG. 13) and further extending inwardly of the bone contacting member into a central region of the implant and extending down a second leg 472 terminating at a second point 492 on an inferior side of peripheral frame portion 200 adjacent to first point 491 from which first support member 470 extends.

As shown in FIG. 11, implant 100 may include a fourth support member 475, including a first leg 476 extending from a first point 493 on a superior side of peripheral frame portion 200 to a bone contacting member (see FIG. 13) and further extending inwardly of the bone contacting member into a central region of the implant and extending down a second leg 477 terminating at a second point 494 on an inferior side of peripheral frame portion 200 adjacent to first point 493 from which first support member 475 extends.

As shown in FIG. 11, third support member 470 and fourth support member 475 may be substantially U-shaped. Also, in some embodiments, the support members may be connected to one another. For example, as shown in FIG. 11, third support member 470 and fourth support member 475 may be connected to one another at the bottoms of the two U-shapes, in an overlapping region 478 in the central region of the implant inward of the bone contacting members.

Figure 12:
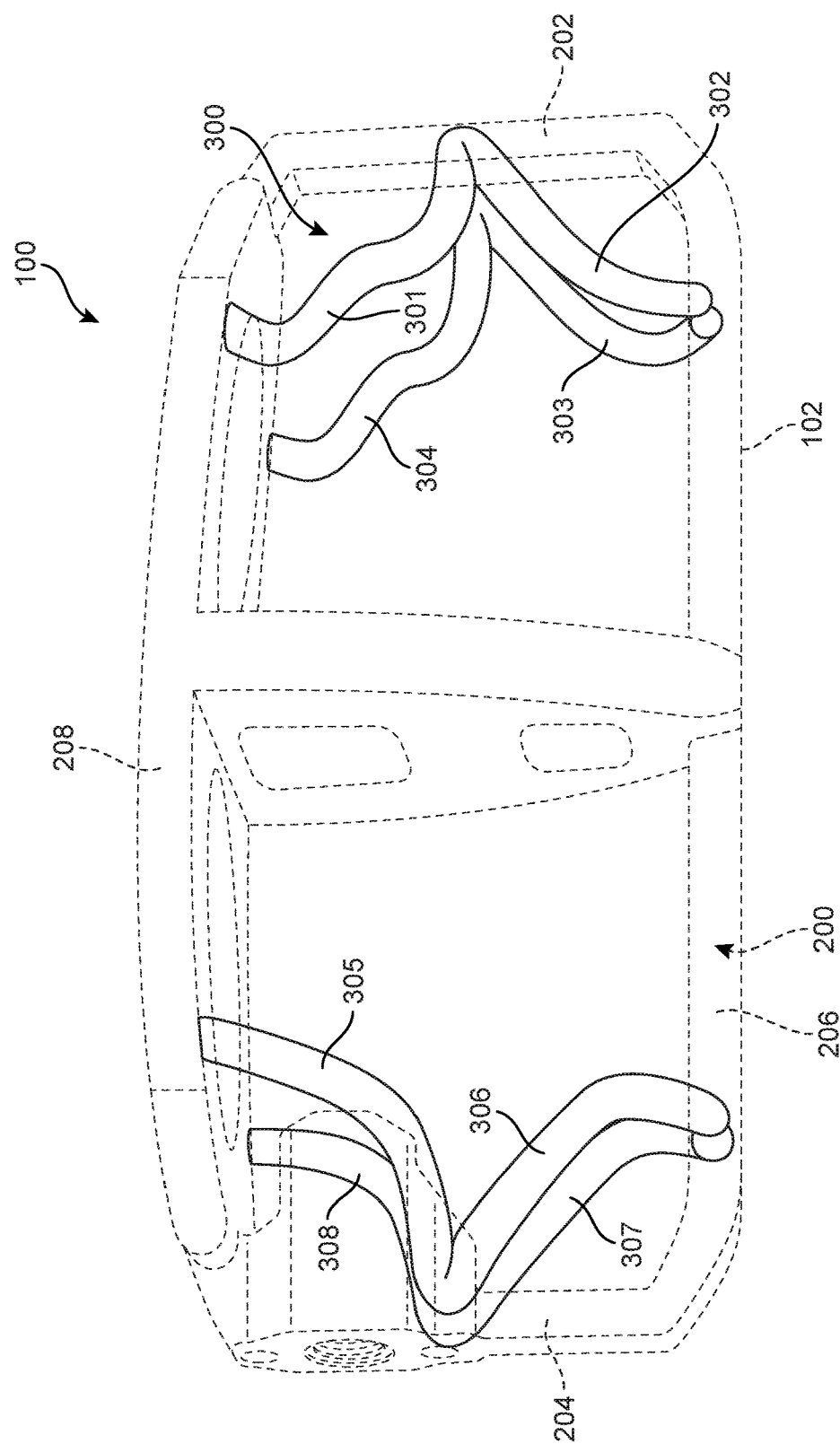
FIG. 12 is a schematic perspective view of a plurality of corner braces arranged within the body of the implant of FIG. 1, with the peripheral frame portion shown in phantom.

Additional structural members may also be provided. For example, in some embodiments, corner braces may be provided to reinforce the implant. FIG. 12 is a schematic perspective view of a plurality of corner braces 300 arranged within the body 102 of implant 100, with peripheral frame portion 200 shown in phantom. As shown in FIG. 12, a first corner brace 301 may extend from vertically oriented peripheral frame portion 208 to first lateral frame portion 202 on an inferior half of implant 100. A second corner brace 302 may extend from first lateral frame portion 202 to posterior frame portion 206 on the inferior half of implant 100. A third corner brace 303 may extend from first lateral frame portion 202 to posterior frame portion 206 on the superior half of the implant. Also, a fourth corner brace 304 may extend from vertically oriented peripheral frame portion 208 to first lateral frame portion 202 on the superior half of implant 100.

At the opposite lateral end of implant 100, a four more corner braces may be arranged similarly. For example, as shown in FIG. 12, a fifth corner brace 305 may extend from vertically oriented peripheral frame portion 208 to first lateral frame portion 202 on an inferior half of implant 100. A sixth corner brace 306 may extend from first lateral frame portion 202 to posterior frame portion 206 on the inferior half of implant 100. A seventh corner brace 307 may extend from first lateral frame portion 202 to posterior frame portion 206 on the superior half of the implant. Also, an eighth corner brace 308 may extend from vertically oriented peripheral frame portion 208 to first lateral frame portion 202 on the superior half of implant 100.

In different embodiments, the sizes, configurations, and orientations of bone contacting members, support members, and/or corner braces could vary.

Figure 13:
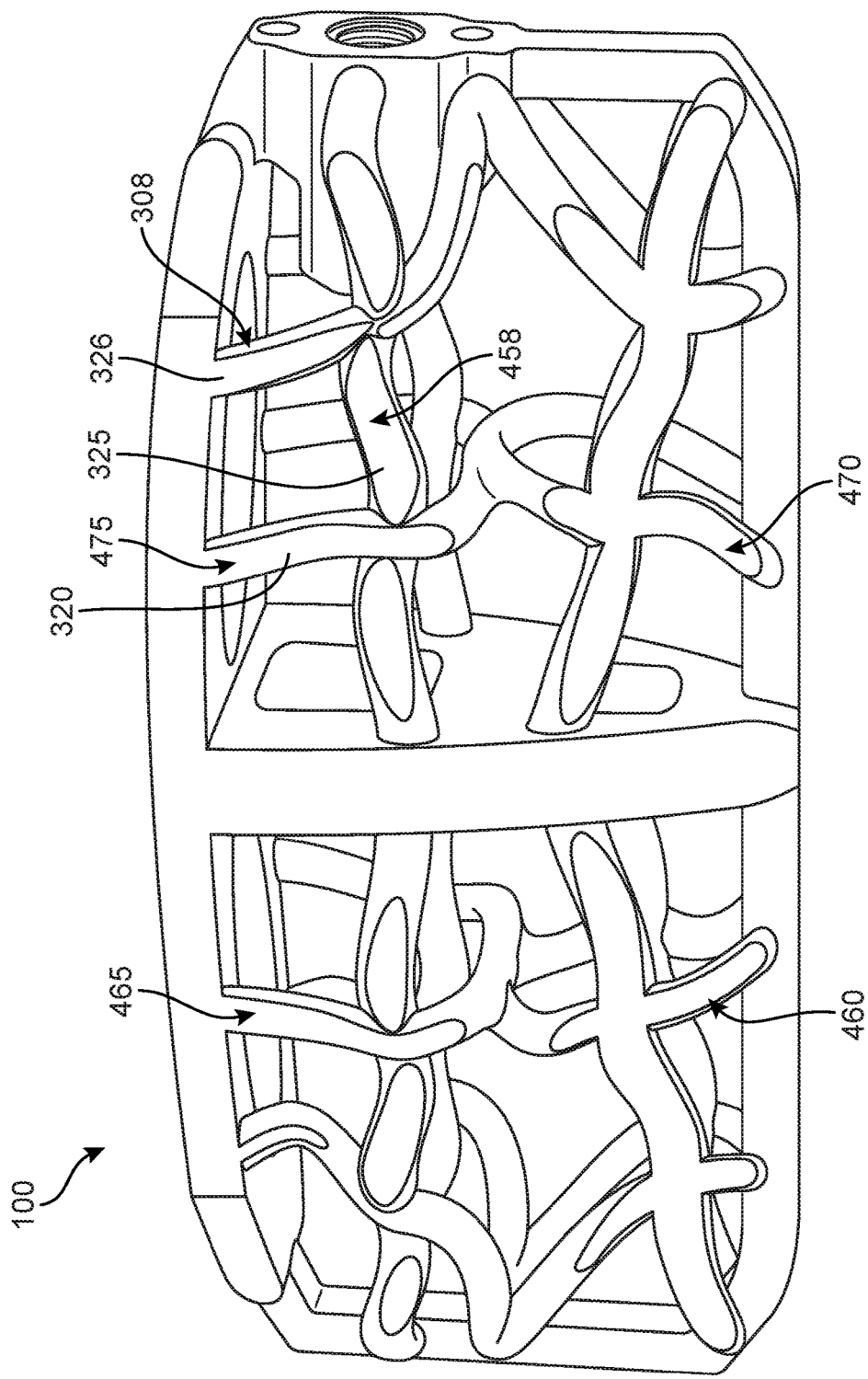
FIG. 13 is a schematic perspective superior view of the implant of FIG. 1, shown with the anterior side facing upward.

FIG. 13 is a schematic perspective superior view of the implant of FIG. 1, shown with the anterior side facing upward. The bone contacting members, support members, and corner braces discussed above can all be seen as arranged and connected to one another in FIG. 13. For example, U-shaped support members 460, 465, 470, and 475 are illustrated in FIG. 13. Also, helical bone contacting member 458 is shown.

In some embodiments, support members and/or corner braces may be disposed distal to bone contacting members, with support members generally disposed further outwards along the superior and inferior sides of an implant. Thus, support members may generally be disposed closer to the vertebral end plates following implantation into the spine. As illustrated in FIG. 13, support member 475 and corner brace 308 both extend to, connect with, and overlap bone contacting member 458.

As shown in FIG. 13, in some embodiments, the structural members may include substantially flattened surfaces to facilitate insertion and bone growth. For example, as shown FIG. 13, bone contacting member 458 may include one or more flattened surfaces 325. These flattened surfaces may be provided by removing peaks of the helical coils. Similarly, support member 475 may include a flattened bone contacting surface 320. Where flattened surfaces 325 and flattened bone contacting surface 320 adjoin, the two surfaces may be substantially flush with one another. Also, corner brace 308 may include at least one flattened surface 326.

Figure 14:
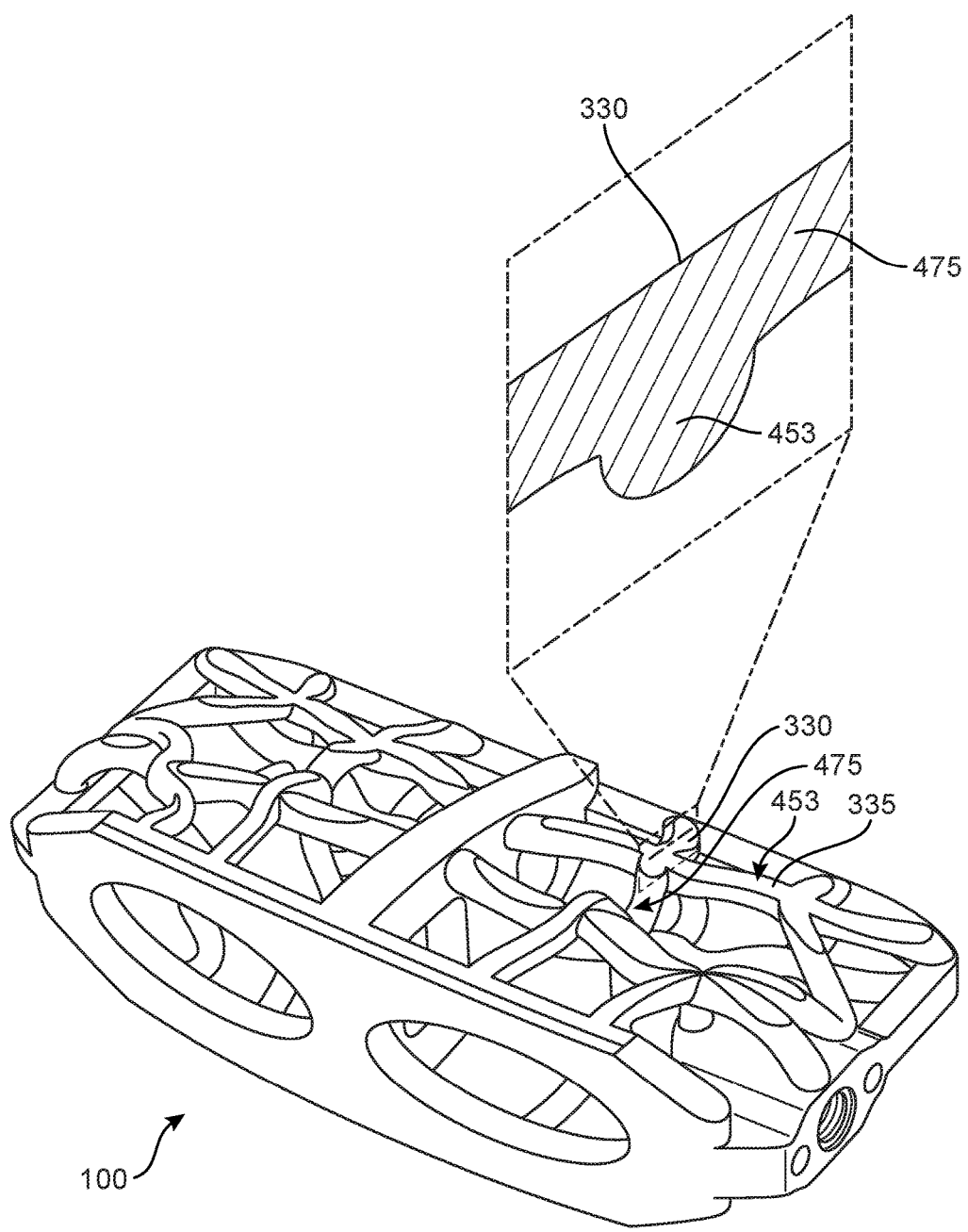
FIG. 14 is a schematic isometric view of the implant of FIG. 1, including an enlarged cut-away view of a structural member.

FIG. 14 illustrates an enlarged cross-sectional view the intersection between support member 475 and bone contacting member 453. As illustrated in FIG. 14, flattened surface 335 of bone contacting member 453 may be substantially flush with flattened surface 330 of support member 475. As also illustrated in FIG. 14, support member 475 overlaps bone contacting member 453 on an outer-facing side of bone contacting member 453.

Bi-Convex Geometry

Figure 15:
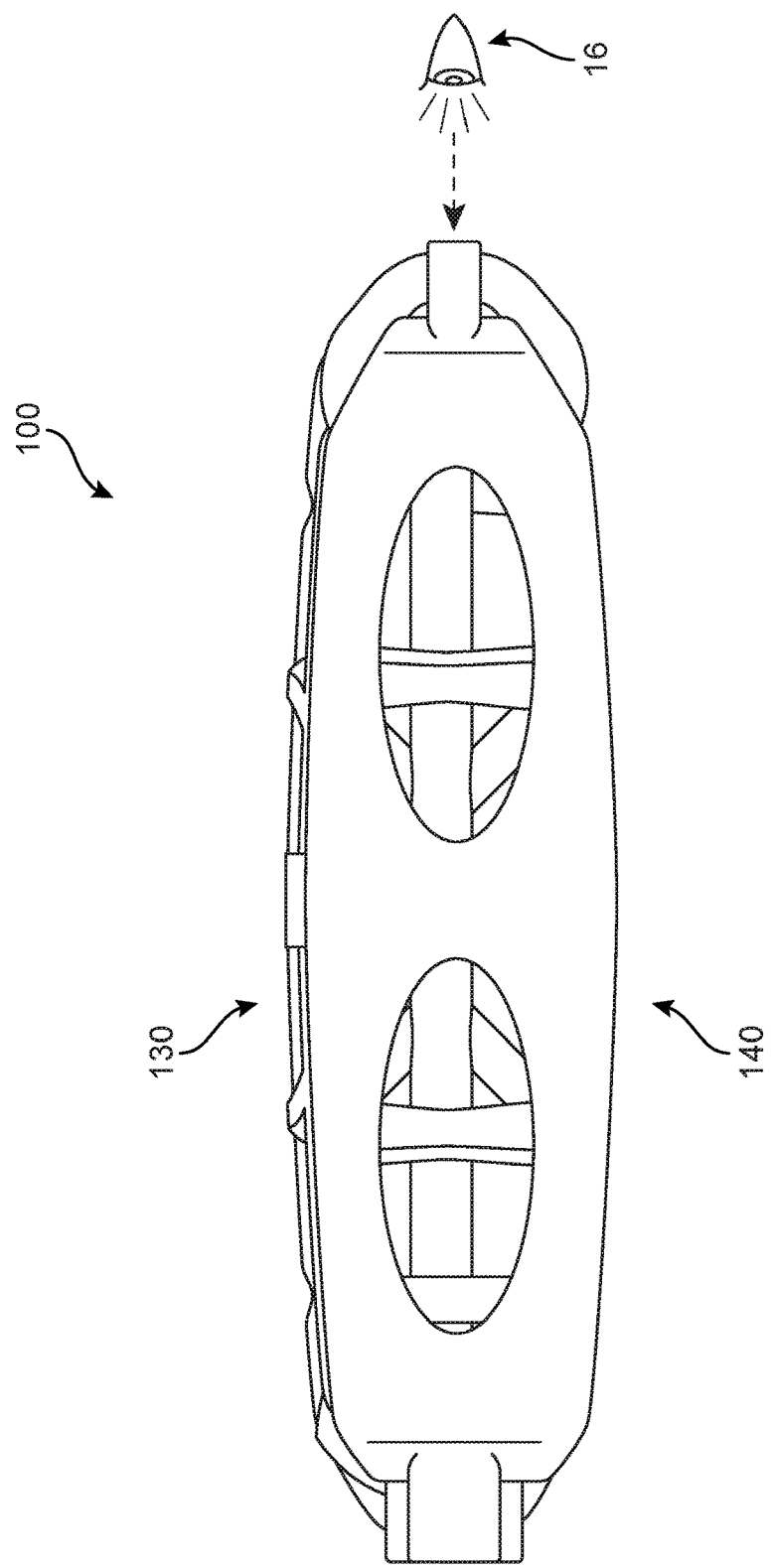
FIG. 15 is a schematic view of the implant of FIG. 1 as viewed from the anterior side.
Figure 16:
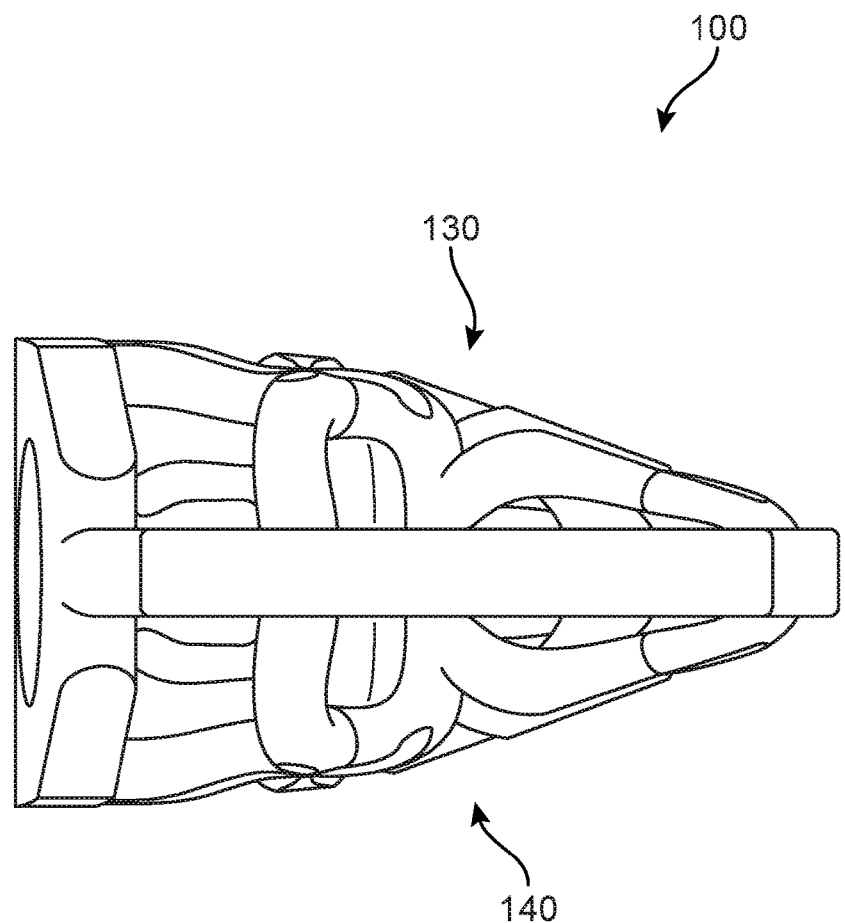
FIG. 16 is a schematic lateral view of the implant of FIG. 1.

FIGS. 15 and 16 provide anterior side and lateral side (or lateral end) views, respectively, of implant 100. As seen in FIGS. 15-16, implant 100 may be configured with a bi-convex geometry. Specifically, implant 130 can be seen to have a convex superior side 130 and a similarly convex inferior side 140. Furthermore, when viewed from the lateral end shown in FIG. 16, implant 100 has an approximately convex shape along superior side 130 and the inferior side 140. Thus, it may be seen that implant 100 is convex in both the longitudinal and lateral directions, which helps to match the geometry of the vertebral endplates. Thus arranging the implant so as to have a convex outer surface on the superior and inferior sides helps to ensure that distal surfaces (i.e., "flattened surfaces") of implant 100 contact the concave surfaces of opposing vertebral plates. In other embodiments, however, the inferior and/or superior surfaces of an implant could be concave, flat, tapered/angulated to provide lordosis or kyphosis, etc. in shape.

In some embodiments, at least one lateral side of an implant may be shaped to facilitate easy insertion. As best seen in FIGS. 15-16, by virtue of the tapered geometry of implant 100, the lateral side of implant 100 is configured as a rounded end to improve ease of insertion. In some cases, this may be referred to as a "bulleted nose" configuration.

Embodiments can also be provided with various flat/parallel (0-degree), lordotic, and hyper-lordotic angles. In some embodiments, the implant can be configured with an approximately 8-degree angle between the superior and inferior surfaces. In other embodiments, the implant can be configured with an approximately 15-degree angle between the superior and inferior surfaces. In still other embodiments, the implant can be configured with an approximately 20-degree angle between the superior and inferior surfaces. Still other angles are possibly including any angles in the range between 0 and 30 degrees. Still other embodiments can provide a lordotic angle of less than 8 degrees. Still other embodiments can provide a hyper-lordotic angle of more than 20 degrees. In at least some embodiments, the lordotic angle of the implant is accomplished via the geometry of the central keel portion and the side frame portion (posterior or anterior).

Figure 17:
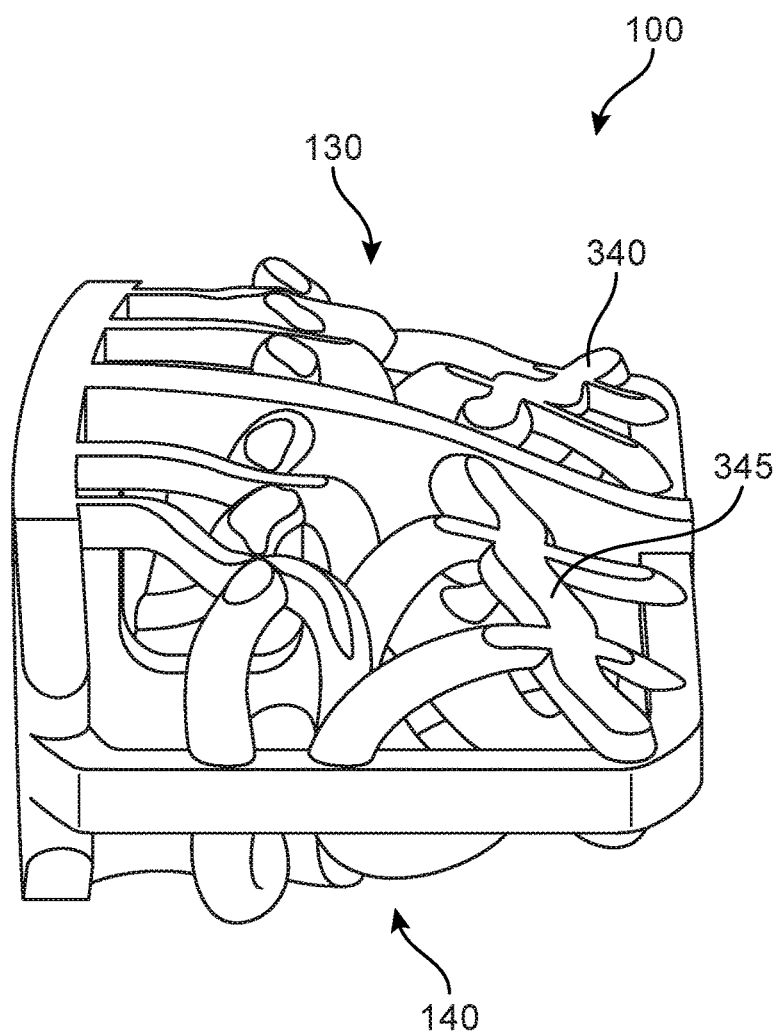
FIG. 17 is a schematic perspective lateral view of the implant of FIG. 1 as viewed from a lateral vantage point indicated by an eye 16 in FIG. 15.

FIG. 17 is a schematic perspective lateral view of the implant of FIG. 1. FIG. 17 further illustrates the bi-convex geometry of implant 100 discussed above. In addition, FIG. 17 also illustrates that the flattened surfaces (e.g., flattened surfaces 340 and 345) of the structural members are generally flush with one another and form the outer surfaces of the implant in one or more sections of the implant. As shown in FIG. 17, these flattened surfaces may be flush with one another along a generally curved surface. This may facilitate implantation as well as bone growth as discussed above.

Open Inner Volume of Implant

The arrangement of structural members with the body may also be designed to achieve a desired total open volume. As used herein a total volume is the combined volume of any openings between structural members, any openings in the body, or between structural members and the body. This open configuration may facilitate bone growth in and through the implant. A portion, or substantially all of, the open spaces is optionally filled with a bone graft or material prior to or after insertion of the implant to facilitate bone growth.

The total volume of the open spaces (also referred to simply as the open space volume) within any particular implant is dependent on the overall dimension of the implant as well as the size and dimension of individual components within the implant including structural members, frame portions, etc. The open space volume may range from about 20% to 80% of the volume of the implant. In some embodiments, implant 100 may have an open space volume that is between 25% and 80% of the implant's total volume. In still further embodiments, implant 100 may have an open space volume that is between 40% and 75% of the total implant volume.

Figure 18:
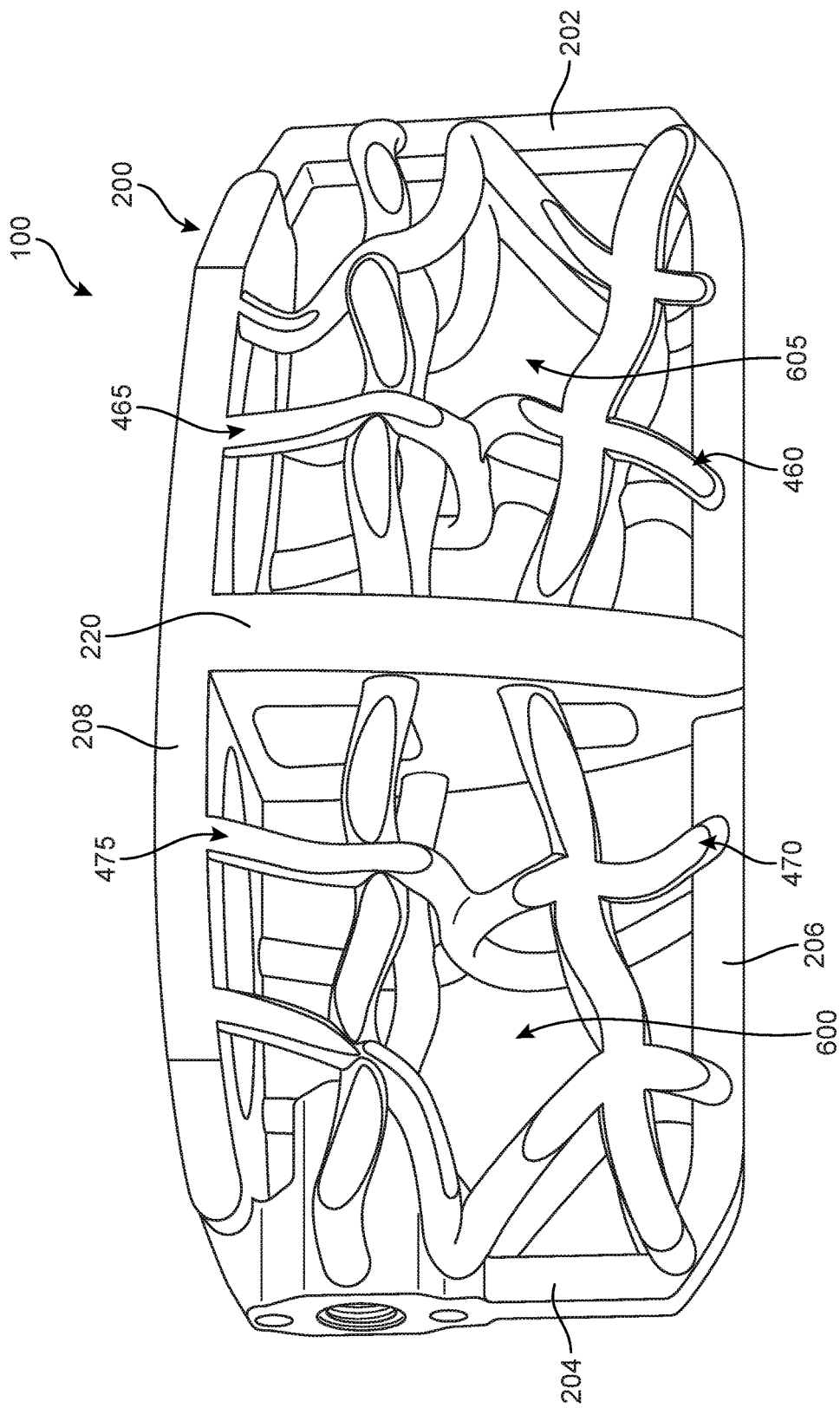
FIG. 18 is a schematic perspective inferior view of the implant of FIG. 1, shown with the anterior side facing upward.
Figure 19:
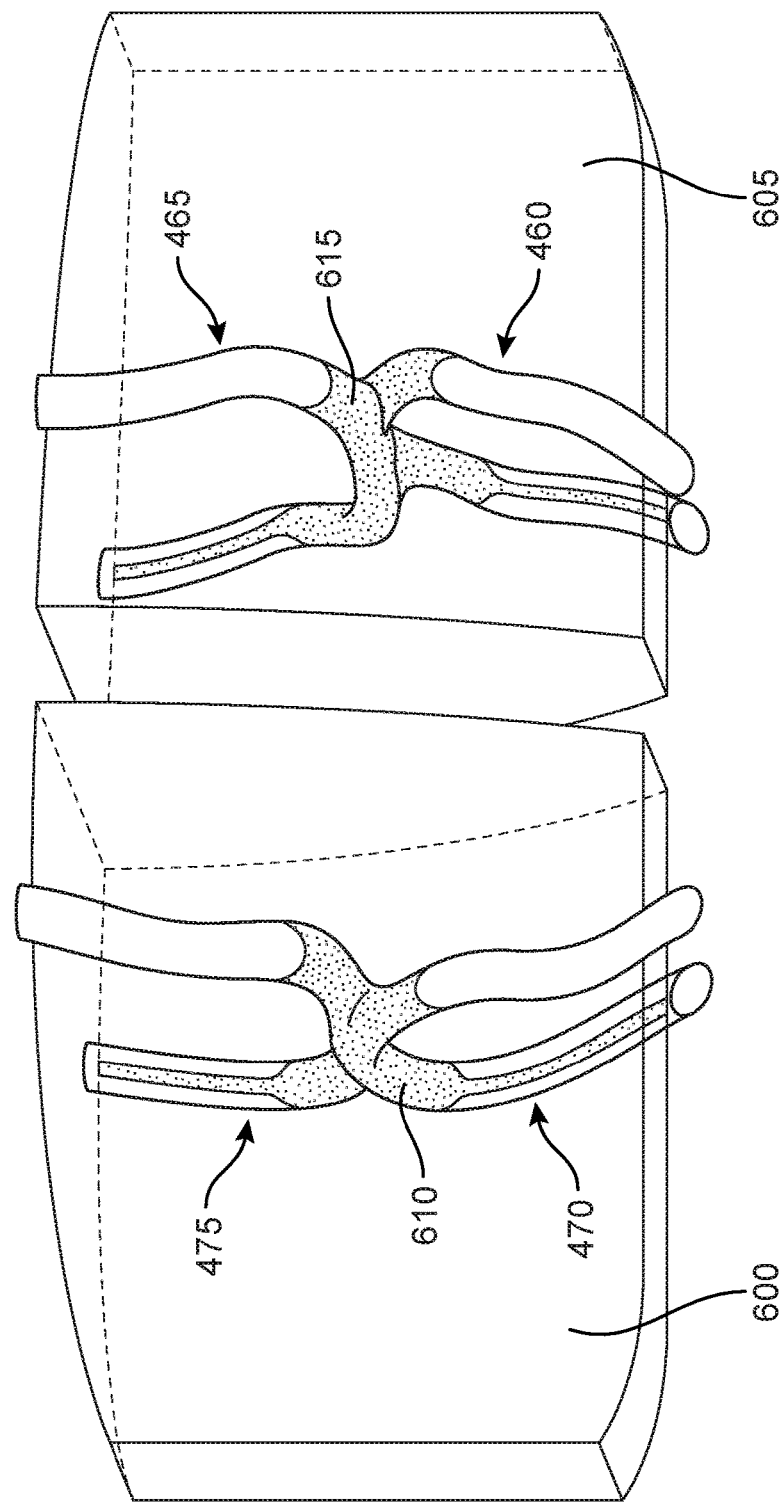
FIG. 19 is a schematic perspective view of the support members of the implant of FIG. 1 as arranged within an inner volume defined within the implant of FIG. 1.
Figure 20:
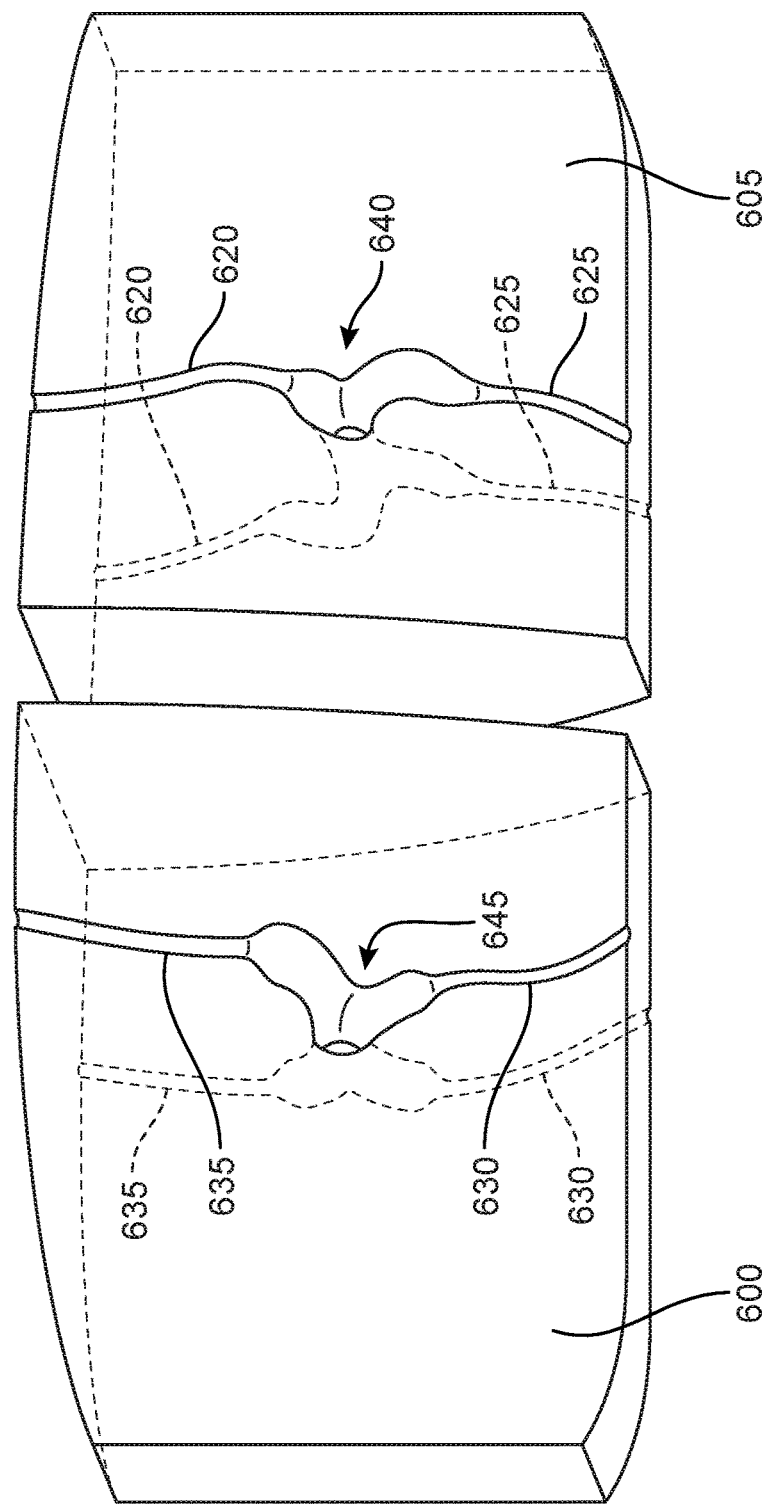
FIG. 20 is a schematic perspective view of the inner volume defined within the implant of FIG. 1 with the support members removed.

Due to reinforcements made to various portions of the implant, the inner volume may be left devoid of structural members except for minimal number of support members. This provides more volume for bone ingrowth material. FIGS. 18-20 illustrate the inner volume of the implant and the configuration of the support members in it.

FIG. 18 is a schematic perspective inferior view of the implant of FIG. 1, shown with the anterior side facing upward. As shown in FIG. 18, implant 100 may include support members 460, 465, 470, and 475. These U-shaped support members may connect to one another in the interior volume or cavity of implant 100. For example, as shown in FIG. 18, central wall 220, posterior frame member 206, lateral frame member 204 and vertical wall member 208 may define a first inner volume 600 in a central region within one half of implant 100. Support member 470 and support member 475 may connect with one another within first volume 600. Similarly, central wall 220, posterior frame member 206, lateral frame member 202 and vertical wall member 208 may define a second inner volume 605 in a central region within the other half of implant 100. Support member 460 and support member 465 may connect with one another within second volume 605.

FIG. 19 is a schematic perspective view of the support members of implant 100 as arranged within the inner volumes defined within implant 100. As shown in FIG. 19, first volume 600 is represented by a complex, three-dimensional geometric shape, as defined above. In FIG. 19, a first stippled region 610 illustrates the portions of support member 470 and support member 475 that extend into first volume 600. Similarly, a second stippled region 615 illustrates the portions of support member 460 and support member 465 that extend into second volume 605.

FIG. 20 is a schematic perspective view of the inner volume defined within implant 100 with the support members removed. As illustrated in FIG. 20, a first pair of channels 630, a second pair of channels 635, and a thru-hole 645 are depicted in the volumetric regions where support members 470 and 475 were located. This represents the vast volume within the first half of implant 100. This volume can be filled with bone ingrowth promoting material, and ultimately filled with bone ingrowth. Similarly, a third pair of channels 625, a fourth pair of channels 620, and a second thru-hole 640 illustrate the volumetric regions where support members 460 and 465 were located. Thus, FIG. 20 depicts the vast volume within the second half of implant 100 that can receive bone ingrowth promoting material and ultimately bone ingrowth.

Implantation

Figure 21:
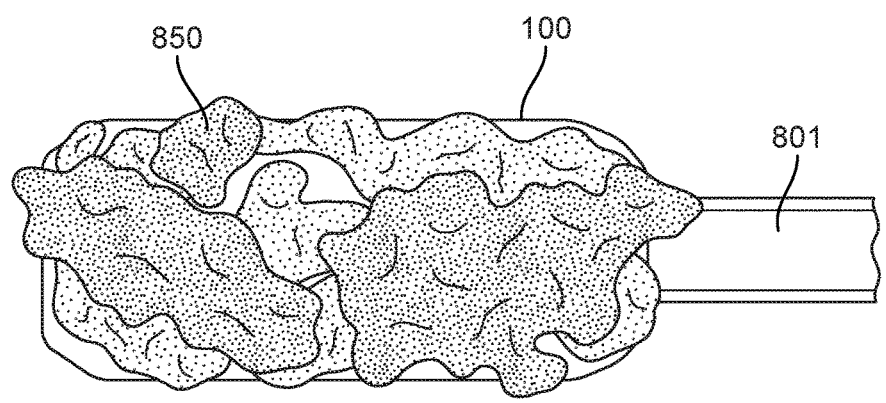
FIG. 21 is a schematic view depicting an implant attached to an implant tool, and where the implant is covered with a bone growth promoting material, according to an embodiment.
Figure 22:
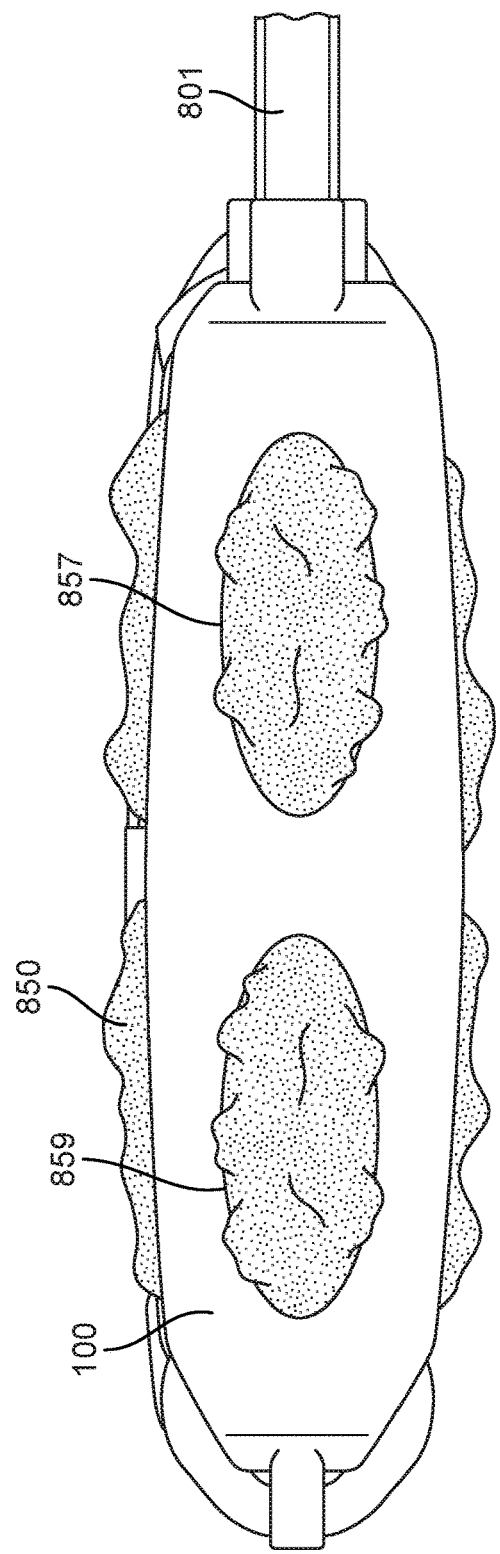
FIG. 22 is a schematic view of the implant of FIG. 17 as viewed from the anterior side and filled with bone growth promoting material.

FIGS. 21-24 illustrate various schematic views of a process of implanting an implant 800. Referring first to FIGS. 21-22, the implantation process may begin with the application of a bone growth promoting material, also referred to as a BGPM, to the implant. As used herein, a "bone growth promoting material" is any material that helps bone growth.

Bone growth promoting materials may include provisions that are freeze dried onto a surface or adhered to the metal through the use of linker molecules or a binder. Examples of bone growth promoting materials are any materials including bone morphogenetic proteins (BMPs), such as BMP-1, BMP-2, BMP-4, BMP-6, and BMP-7. These are hormones that convert stem cells into bone forming cells. Further examples include recombinant human BMPs (rhBMPs), such as rhBMP-2, rhBMP-4, and rhBMP-7. Still further examples include platelet derived growth factor (PDGF), fibroblast growth factor (FGF), collagen, BMP mimetic peptides, as well as RGD peptides. Generally, combinations of these chemicals may also be used. These chemicals can be applied using a sponge, matrix or gel.

Some bone growth promoting materials may also be applied to an implantable prosthesis through the use of a plasma spray or electrochemical techniques. Examples of these materials include, but are not limited to, hydroxyapatite, beta tri-calcium phosphate, calcium sulfate, calcium carbonate, as well as other chemicals.

A bone growth promoting material can include, or may be used in combination with a bone graft or a bone graft substitute. A variety of materials may serve as bone grafts or bone graft substitutes, including autografts (harvested from the iliac crest of the patient's body), allografts, demineralized bone matrix, and various synthetic materials.

Some embodiments may use autograft. Autograft provides the spinal fusion with calcium collagen scaffolding for the new bone to grow on (osteoconduction). Additionally, autograft contains bone-growing cells, mesenchymal stem cells and osteoblast that regenerate bone. Lastly, autograft contains bone-growing proteins, including bone morphogenic proteins (BMPs), to foster new bone growth in the patient.

Bone graft substitutes may comprise synthetic materials including calcium phosphates or hydroxyapatites, stem cell containing products which combine stem cells with one of the other classes of bone graft substitutes, and growth factor containing matrices such as INFUSE® (rhBMP-2-containing bone graft) from Medtronic, Inc.

It should be understood that the provisions listed here are not meant to be an exhaustive list of possible bone growth promoting materials, bone grafts or bone graft substitutes.

In some embodiments, BGPM may be applied to one or more outer surfaces of an implant. In other embodiments, BGPM may be applied to internal volumes within an implant. In still other embodiments, BGPM may be applied to both external surfaces and internally within an implant. As seen in FIGS. 21-22, a BGPM 850 has been placed inside an interior of implant 800 and also applied on superior and inferior surfaces of implant 800. Moreover, as shown in FIG. 22, BGPM 850 has been inserted through (and extends through) a first window 857 and a second window 859 of implant 800.

As shown in FIG. 22, a method of inserting implant 100 may include filling the inner volume of implant 100 with bone growth promoting material around the support members.

Figure 23:
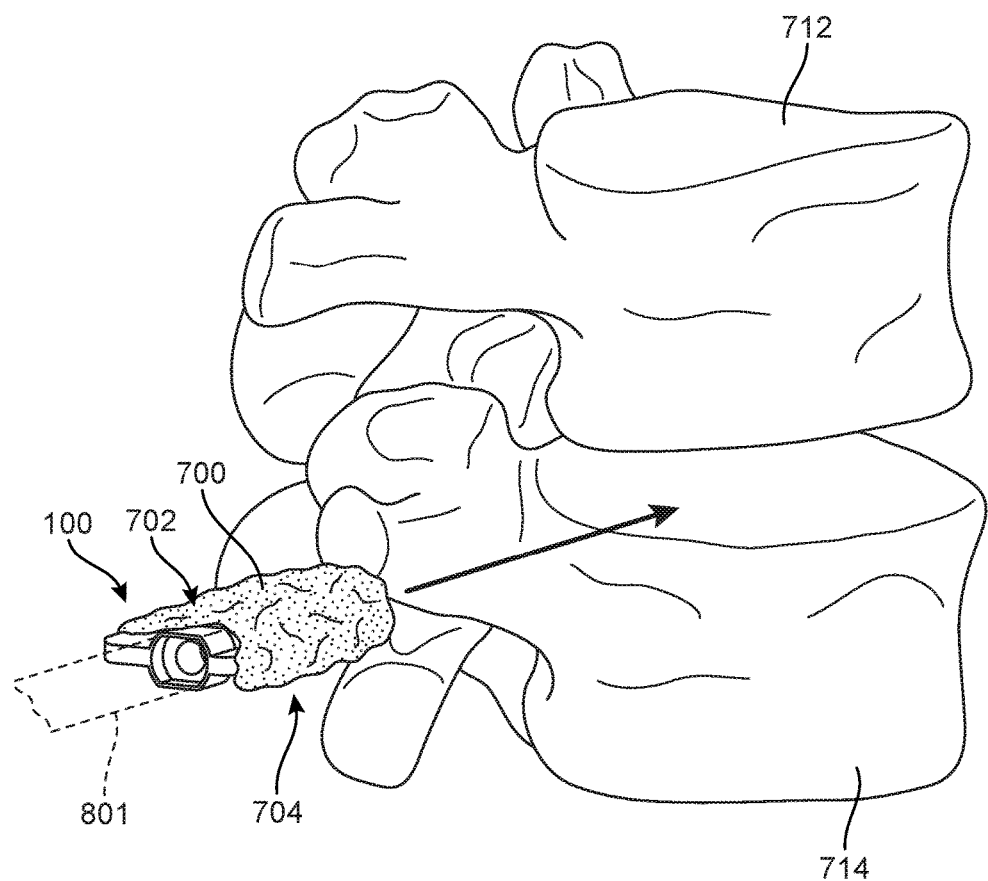
FIG. 23 is a schematic isometric view of an implant being positioned for insertion between two vertebrae, according to an embodiment.
Figure 24:
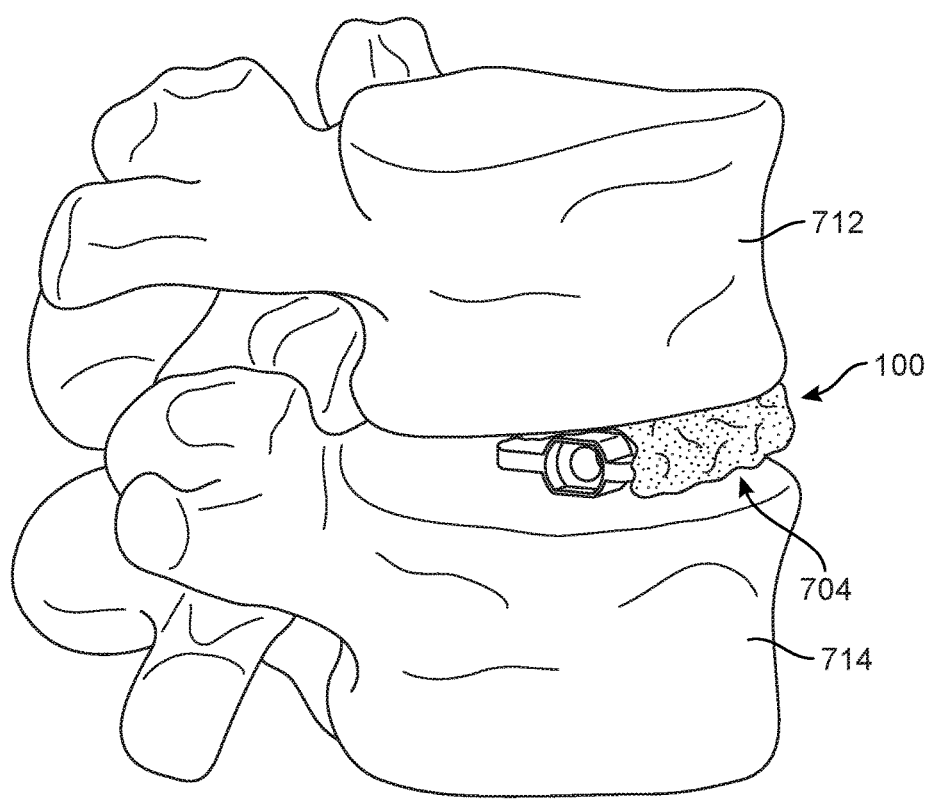
FIG. 24 is a schematic isometric view of the implant of FIG. 18 inserted between the two vertebrae.

FIGS. 23 and 24 show schematic views of the implant pre-implantation (FIG. 23) and post-implantation (FIG. 24). Once implanted, implant 800 may be disposed between, and in direct contact with, adjacent vertebra. Specifically, a superior side 702 of implant 600 is disposed against first vertebra 712. Likewise, an inferior side 704 of implant 600 is disposed against second vertebra 714.

In different embodiments, implantation methods could vary. In some embodiments, implant 800 may be secured to an implantation tool 701 (partially seen in FIGS. 21-22) that is used to drive implant 800 into the spine. Implantation tool 701 could be any rod, ram, pole or other device that can be hammered, rammed, or otherwise driven to position implant 800 between adjacent vertebrae. As previously mentioned, in some cases, an implantation tool could be attached to implant 800 at a fastener receiving portion (i.e., a threaded opening for receiving a threaded shaft from a tool).

The implants for use in the spine have overall dimensions suitable for insertion in the spine, typically between two vertebral bodies. The shape of the implant and dimensions depends on the site into which it is inserted. Exemplary heights for implants such as implant 100 and implant 600 include, but are not limited to, 5 mm to 30 mm. Other embodiments could have incremental heights of any value in the range between the aforementioned range, most often between 8 mm and 16 mm. Still other embodiments could have a height greater than 16 mm. Still other embodiments could have a height less than 8 mm. Additionally, the horizontal footprint of the implant could vary. Exemplary footprint sizes for any embodiments of the implant include, but are not limited to, 15-20 mm in the anterior-posterior direction and 40-60 mm in the lateral-lateral direction. Still other embodiments could be configured with any other footprint sizes.

The dimensions of one or more structural members could vary. In some embodiments, a structural member could have a cross-sectional diameter in a range between 0.2 and 3 mm. For structural members with polygonal cross sections, the dimensions characterizing the polygon (e.g., first and second diameters for an ellipse) could vary. As an example, a structural member with an elliptic cross section could have a cross section with a first diameter in a range between 0.2 mm and 3 mm and a second diameter in range between 0.2 mm and 3 mm. In other embodiments, a structural member could have any other cross-sectional diameter. Moreover, in some cases a bone contacting member and a support member could have similar cross-sectional diameters while in other cases a bone contacting member and a support member could have different cross-sectional diameters.

The various components of an implant may be fabricated from biocompatible materials suitable for implantation in a human body, including but not limited to, metals (e.g. titanium or other metals), synthetic polymers, ceramics, and/or their combinations, depending on the particular application and/or preference of a medical practitioner.

Generally, the implant can be formed from any suitable biocompatible, non-degradable material with sufficient strength. Typical materials include, but are not limited to, titanium, biocompatible titanium alloys (e.g. γTitanium Aluminides, $Ti_6$—$Al_4$—V ELI (ASTM F 136 and F 3001), or $Ti_6$—$Al_4$—V (ASTM F 2989, F 1108 and ASTM F 1472)) and inert, biocompatible polymers, such as polyether ether ketone (PEEK) (e.g. PEEK-OPTIMA®, Invibio Inc and Zeniva Solvay Inc.). Optionally, the implant contains a radiopaque marker to facilitate visualization during imaging.

In different embodiments, processes for making an implant can vary. In some embodiments, the entire implant may be manufactured and assembled via readditional/CNC machining, injection-molding, casting, insert-molding, co-extrusion, pultrusion, transfer molding, overmolding, compression molding, 3-Dimensional (3-D) printing (including Direct Metal Laser Sintering and Electron Beam Melting), dip-coating, spray-coating, powder-coating, porous-coating, milling from a solid stock material and their combinations. Moreover, the embodiments can make use of any of the features, parts, assemblies, processes and/or methods disclosed in the "The Coiled Implant Application".

While various embodiments have been described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. An implant, comprising:
a body;
the body defining a transverse plane dividing the implant into a superior half and an inferior half;
a peripheral frame portion defining a periphery of the body;
a central wall extending from a first side of the peripheral frame portion to a second side of the peripheral frame portion;
a first helical bone contacting member attached to the body and disposed within the superior half of the implant;
a second helical bone contacting member attached to the body and disposed within the superior half of the implant;
a first support member extending from a first point on a superior side of the peripheral frame portion to the first the bone contacting member and further extending inwardly of the bone contacting member into a central region of the implant and terminating at a second point on an inferior side of the peripheral frame portion adjacent to the first point from which the first support member extends; and
a second support member extending from a third point on the peripheral frame portion opposite the first point to the second helical bone contacting member and further extending inwardly of the bone contacting members and terminating at a fourth point on the peripheral frame portion;
wherein the first support member and the second support member are substantially U-shaped and are connected to one another at the bottoms of the two U-shapes in the central region of the implant inward of the bone contacting members.

2. The implant of claim 1, further comprising:
a third helical bone contacting member attached to the body and disposed within the superior half of the implant and located on an opposite side of the central wall from the first helical bone contacting member;
a fourth helical bone contacting member attached to the body and disposed within the superior half of the implant and located on an opposite side of the central wall from the second helical bone contacting member;
wherein the third helical bone contacting member is disposed on the first side of the implant and the fourth helical bone contacting member is disposed on the second side of the implant;
a third support member extending from a fifth point on a superior side of the peripheral frame portion to the third helical bone contacting member and further extending inwardly of the third helical bone contacting member into the central region of the implant and terminating at a sixth point on an inferior side of the peripheral frame portion adjacent to the fifth point from which the third support member extends; and
a fourth support member extending from a seventh point on the peripheral frame portion opposite the fifth point to the fourth helical bone contacting member and further extending inwardly of the bone contacting members and terminating at an eighth point on the peripheral frame portion;
wherein the fifth point and the sixth point on the peripheral frame portion are disposed on the first side of the implant and the seventh point and the eighth point are disposed on the second side of the implant.

3. The implant of claim 2, wherein the third support member and the fourth support member are connected to one another in the central region inward of the bone contacting members.

4. The implant of claim 3, wherein the third support member and the fourth support member are substantially U-shaped and are connected to one another at the bottoms of the two U-shapes in the central region of the implant inward of the bone contacting members.

5. The implant of claim 2, wherein at least one of the first support member and the second support member includes a bone contacting portion.

6. The implant of claim 1, wherein the central region of the implant is devoid of structural members except for the first support member and the second support member.

7. The implant of claim 1, wherein the peripheral frame portion includes a first side, a second side opposite the first side, a third side extending substantially perpendicular to the first side, and a fourth side opposite the third side; the first side, second side, third side, and fourth side defining the periphery of the implant;
the first helical bone contacting member extending from the central wall to the third side of the peripheral frame portion in the superior half of the implant, and the second helical bone contacting member extending from the central wall to the third side of the peripheral frame portion in the superior half of the implant;
wherein the first helical bone contacting member and the second helical bone contacting member converge toward one another proximate the central wall.

8. The implant of claim 7, further including a third helical bone contacting member attached to the body and disposed within the superior half of the implant;
the third helical bone contacting member extending from the central wall to the fourth side of the peripheral frame portion in the superior half of the implant, and the fourth helical bone contacting member extending from the central wall to the fourth side of the peripheral frame portion in the superior half of the implant;
wherein the third helical bone contacting member and the fourth helical bone contacting member converge toward one another proximate the central wall.

9. The implant of claim 1, wherein the first support member overlaps the first bone contacting member on an outer-facing side of the first bone contacting member.

10. The implant of claim 1, wherein the first bone contacting member is attached to the central wall and extends to the peripheral frame portion.

11. An implant, comprising:
a body including a peripheral frame portion including a first side, a second side opposite the first side, a third side extending substantially perpendicular to the first side, and a fourth side opposite the third side; the first side, second side, third side, and fourth side defining a periphery of the implant;
a central wall extending from the first side of the peripheral frame portion to the second side of the peripheral frame portion; and
a plurality of helical bone contacting members extending from the central wall of the body to the peripheral frame portion and defining outer surfaces of the implant; and
a first support member and a second support member that extend into the central region of the implant on a first side of the central wall;
wherein, on the first side of the central wall, the peripheral frame portion, the central wall, and the plurality of helical bone contacting members define an inner volume in a central region of the implant;
wherein the central region of the implant is devoid of structural members except for the first support member and the second support member;
the plurality of helical bone contacting members including a first helical bone contacting member extending from the central wall to the third side of the peripheral frame portion in a superior half of the implant, and a second helical bone contacting member extending from the central wall to the third side of the peripheral frame portion in the superior half of the implant;
wherein the first helical bone contacting member and the second helical bone contacting member converge toward one another proximate the central wall.

12. The implant of claim 11, wherein the first support member and the second support member are substantially U-shaped and are connected to one another at the bottoms of the two U-shapes in the central region of the implant.

13. The implant of claim 11, wherein the first support member includes a first bone contacting portion and the second support member includes a second bone contacting portion.

14. The implant of claim 13, wherein bone contacting portions of the plurality of helical bone contacting members, the first bone contacting portion of the first support member, and the second bone contacting portion of the second support member include substantially planar surfaces that are disposed substantially flush with one another to form the outer surfaces of the implant in one section of the implant.

15. The implant of claim 11, wherein the first support member overlaps at least a first bone contacting member of the plurality of helical bone contacting members on an outer-facing side of the first bone contacting member.

16. The implant of claim 11, wherein the plurality of helical bone contacting members further includes a third helical bone contacting member extending from the central wall to the fourth side of the peripheral frame portion in the superior half of the implant, and a fourth helical bone contacting member extending from the central wall to the fourth side of the peripheral frame portion in the superior half of the implant;
wherein the third helical bone contacting member and the fourth helical bone contacting member converge toward one another proximate the central wall.

17. A method of fusing two vertebrae of a spinal column, comprising:
providing an implant, including:
a body defined by a peripheral frame portion;
a central wall extending from a first side of the peripheral frame portion to a second side of the peripheral frame portion; and
a plurality of bone contacting members extending from the central wall of the body to the peripheral frame portion and defining outer surfaces of the implant; and
a first support member and a second support member that extend into the central region of the implant on a first side of the central wall;
wherein, on the first side of the central wall, the peripheral frame portion, the central wall, and the plurality of bone contacting members define an inner volume in a central region of the implant; and
wherein the central region of the implant is devoid of structural members except for the first support member and the second support member;
wherein at least one of the plurality of bone contacting members is helical;
wherein the first support member and the second support member are connected to one another in the central region inward of the bone contacting members; and
wherein the first support member and the second support member are substantially U-shaped and are connected to one another at the bottoms of the two U-shapes in the central region of the implant inward of the bone contacting members;
the method further including filling the inner volume of the implant with bone growth promoting material around the first support member and the second support member; and
inserting the implant between two vertebrae of a spinal column.

18. The method of claim 17, wherein the peripheral frame portion of the implant includes a first side, a second side opposite the first side, a third side extending substantially perpendicular to the first side, and a fourth side opposite the third side, the first side, second side, third side, and fourth side defining the periphery of the implant;
the first helical bone contacting member extending from the central wall to the third side of the peripheral frame portion in a superior half of the implant, and the second helical bone contacting member extending from the central wall to the third side of the peripheral frame portion in the superior half of the implant;
wherein the first helical bone contacting member and the second helical bone contacting member converge toward one another proximate the central wall.

19. The method of claim 17, wherein the first support member overlaps at least a first bone contacting member of the plurality of bone contacting members on an outer-facing side of the first bone contacting member.

20. The method of claim 17, wherein each of the plurality of bone contacting members have a generalized helical geometry.

* * * * *